US009618518B2

(12) United States Patent
Fauconnier et al.

(10) Patent No.: US 9,618,518 B2
(45) Date of Patent: Apr. 11, 2017

(54) MAGNETIC IMMUNODIAGNOSTIC METHODS AND KIT FOR THE DEMONSTRATION OF ANTIBODY/ANTIGEN COMPLEXES IN ERYTHROCYTE BLOOD GROUPING AND PHENOTYPING

(75) Inventors: Laurence Fauconnier, Villeneuve d'Ascq (FR); Yves Barbreau, Mouvaux (FR); Arnaud Boulet, La Neuveville (CH); Maha Zakhour, Lille (FR)

(73) Assignee: DIAGAST, Loos (FR)

( * ) Notice: Subject to any disclaimer, the term of this patent is extended or adjusted under 35 U.S.C. 154(b) by 315 days.

(21) Appl. No.: 13/810,925

(22) PCT Filed: Jul. 21, 2011

(86) PCT No.: PCT/EP2011/062560
§ 371 (c)(1),
(2), (4) Date: Jan. 18, 2013

(87) PCT Pub. No.: WO2012/010666
PCT Pub. Date: Jan. 26, 2012

(65) Prior Publication Data
US 2013/0130280 A1    May 23, 2013

Related U.S. Application Data

(60) Provisional application No. 61/409,393, filed on Nov. 2, 2010.

(30) Foreign Application Priority Data

Jul. 21, 2010 (FR) ..................... 10 55973

(51) Int. Cl.
*G01N 33/553* (2006.01)
*G01N 33/68* (2006.01)
(Continued)

(52) U.S. Cl.
CPC ......... *G01N 33/68* (2013.01); *G01N 33/5434* (2013.01); *G01N 33/54326* (2013.01);
(Continued)

(58) Field of Classification Search
CPC ............. G01N 33/54326; G01N 33/80; G01N 33/555; G01N 33/54333
See application file for complete search history.

(56) References Cited

U.S. PATENT DOCUMENTS 4,560,647 A    12/1985 Stocker
4,672,040 A *   6/1987 Josephson ............... 436/526
(Continued)

FOREIGN PATENT DOCUMENTS

EP    0058780 A1    9/1982
EP    0194212 A1    9/1986
(Continued)

OTHER PUBLICATIONS

B. Gardner, S.F. Parsons, A.H. Merry, D.J. Anstee, "Epitopes on sialoglycoprotein alpha: evidence for heterogeneity in the molecule", Immunology, 1989, 68, 283-289.*
(Continued)

*Primary Examiner* — Chris L Chin
(74) *Attorney, Agent, or Firm* — Birch, Stewart, Kolasch & Birch, LLP

(57) ABSTRACT

The current invention relates to a magnetic immunodiagnostic method for the demonstration of antibody/antigen complexes of blood group and phenotype. Such a method involves the research and/or identification of antibodies or antigens, preferably anti-antigen antibodies or antigens of a blood group. This method implements a suspension of magnetic particles coated with an antibody anti-glycophorin A that can recognize and specifically magnetize erythro- (Continued)

Figure 1A:
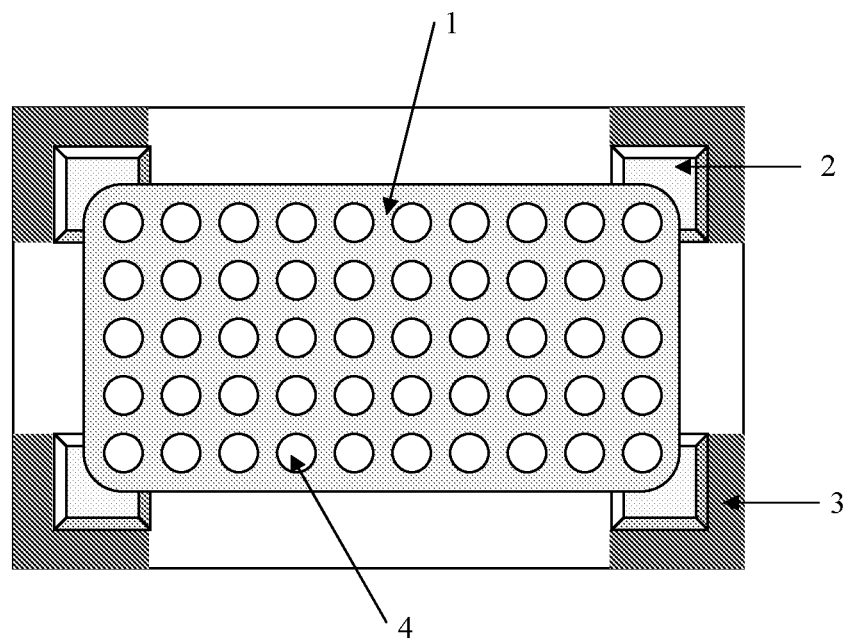

cytes. The invention also includes a device and kit for carrying out one such method.

7 Claims, 12 Drawing Sheets

(51) Int. Cl.
    *G01N 33/543*     (2006.01)
    *G01N 33/80*     (2006.01)

(52) U.S. Cl.
    CPC ... *G01N 33/54393* (2013.01); *G01N 33/6854* (2013.01); *G01N 33/80* (2013.01)

(56) References Cited

U.S. PATENT DOCUMENTS

| | | | |
|---|---|---|---|
| 4,752,563 A * | 6/1988 | Kortright et al. | 435/7.24 |
| 5,318,914 A | 6/1994 | Matte et al. | |
| 2004/0063163 A1 | 4/2004 | Buffiere et al. | |
| 2005/0266433 A1* | 12/2005 | Kapur et al. | 435/6 |
| 2009/0269776 A1 | 10/2009 | Barbreau et al. | |
| 2011/0207151 A1 | 8/2011 | Barbreau et al. | |

FOREIGN PATENT DOCUMENTS

| | | |
|---|---|---|
| EP | 0230768 A1 | 8/1987 |
| EP | 0351857 A2 | 1/1990 |
| EP | 0426170 A1 | 5/1991 |
| EP | 0528708 A1 | 2/1993 |
| EP | 0755719 A2 | 1/1997 |
| WO | WO 92/17781 A1 | 10/1992 |
| WO | WO 96/09409 A1 | 3/1996 |
| WO | WO 98/02752 A1 | 1/1998 |
| WO | WO 00/73794 A2 | 12/2000 |
| WO | WO 02/46758 A1 | 6/2002 |
| WO | WO 2005/121805 A2 | 12/2005 |
| WO | WO 2007/051844 A1 | 5/2007 |
| WO | WO 2007/092028 A2 | 8/2007 |

OTHER PUBLICATIONS

Bouix et al., "Erythrocyte-magnetized technology: an original and innovative method for blood group serology," Transfusion, vol. 48, Sep. 2008, pp. 1878-1885, XP-002657699.

French Search Report and Written Opinion for French Application No. 1055973, mailed Mar. 21, 2011.

International Search Report and the Written Opinion of the International Searching Authority for International Application No. PCT/EP2011/062560 dated Sep. 9, 2011.

* cited by examiner

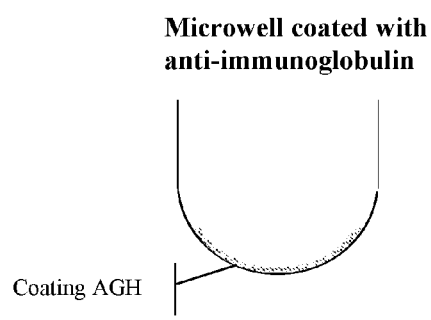
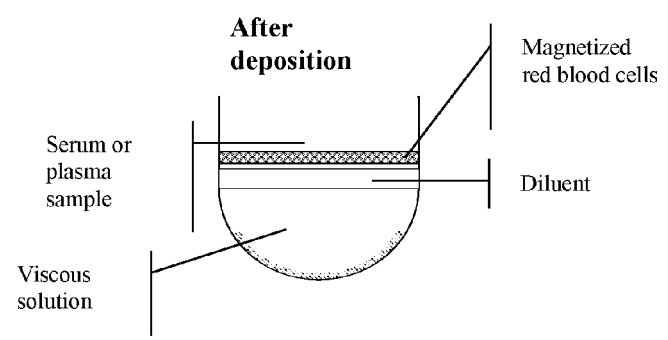
FIGURE 2A  FIGURE 2B
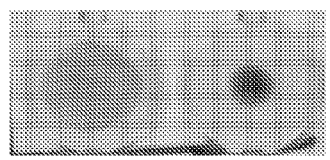
**Positive  Negative
Reaction  Reaction**
FIGURE 3

|  | Anti-D,C,E 1/2 | Anti-D,C,E 1/4 | Anti-D,C,E 1/8 | Anti-D,C,E 1/16 | Anti-D,C,E 1/32 | Anti-D,C,E 1/64 | Anti-D,C,E 1/128 | AB Plasma |
|---|---|---|---|---|---|---|---|---|
| Expected results | 3+ | 3+ | 3+ | 2+ | 2+ | 2+ | 2+ | Neg |
| Results obtained on O RBC panel | | | | | | | | |
| Results obtained on O RBC patient | | | | | | | | |

FIGURE 4

| Anti-D | RBC O1 (R1R1) | RBC O2 (R2R2) | RBC O3 (rr) |
|---|---|---|---|
| Anti-D 20 ng/ml | | | |
| Anti-D 10 ng/ml | | | |
| Anti-D 5 ng/ml | | | |
| Anti-D 2,5 ng/ml | | | |
| Anti-D 1,25 ng/ml | | | |
| Negative | | | |

FIGURE 5

| Patient plasma or serum | RBC Donor | Expected results | Obtained results | Compatibility |
|---|---|---|---|---|
| Anti- D+C+E | O (DCee) | 3+ | | Incompatibility |
| | O (DCcEe) | 3+ | | Incompatibility |
| Anti-K | O (DCee) | Neg | | Compatibility |
| | O (DCcEe) | Neg | | Compatibility |
| Anti-E | O (DCee) | Neg | | Compatibility |
| | O (DCcEe) | 1+ | | Incompatibility |
| AntiJka | O (DCee) | Neg | | Compatibility |
| | O (DCcEe) | 1+ | | Incompatibility |

FIGURE 6

| Patient Plasma or serum | RBC Donor | Expected results | Obtained results | Compatibility |
|---|---|---|---|---|
| Patient # 1 | O 1 | Neg | 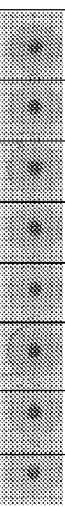 | Compatibility |
| Patient # 2 | O 2 | Neg | 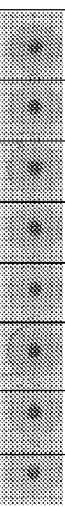 | Compatibility |
| Patient #3 | O 3 | Neg | 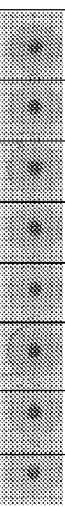 | Compatibility |
| Patient # 4 | O 4 | Neg | 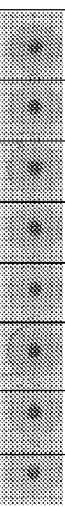 | Compatibility |
| Patient # 5 | O 5 | Neg | 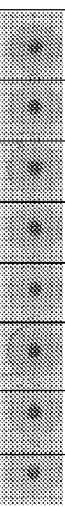 | Compatibility |
| Patient # 6 | O 6 | Neg | 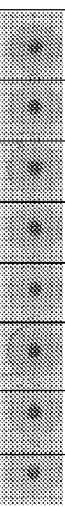 | Compatibility |
| Patient # 7 | O 7 | Neg | 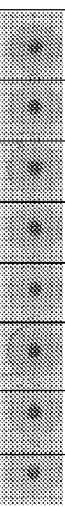 | Compatibility |
| Patient # 8 | O 8 | Neg | 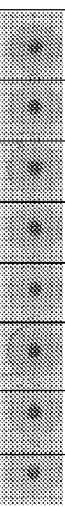 | Compatibility |
FIGURE 7

1st magnetization method

2nd magnetization method

3rd magnetization method

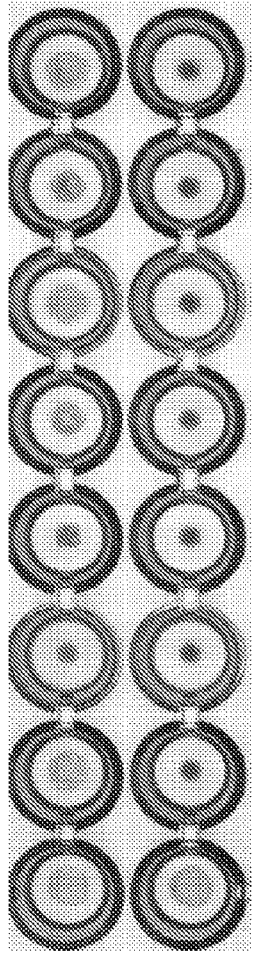 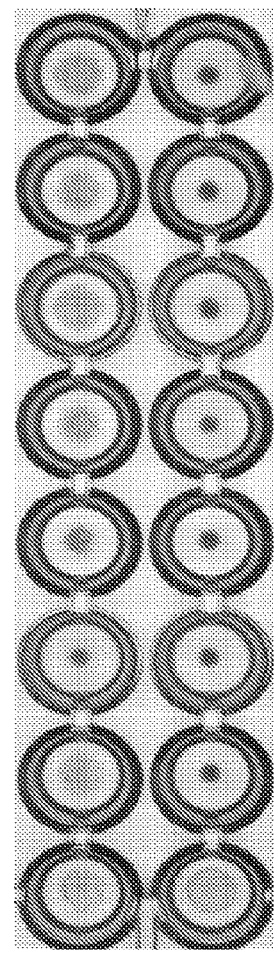
FIGURE 17

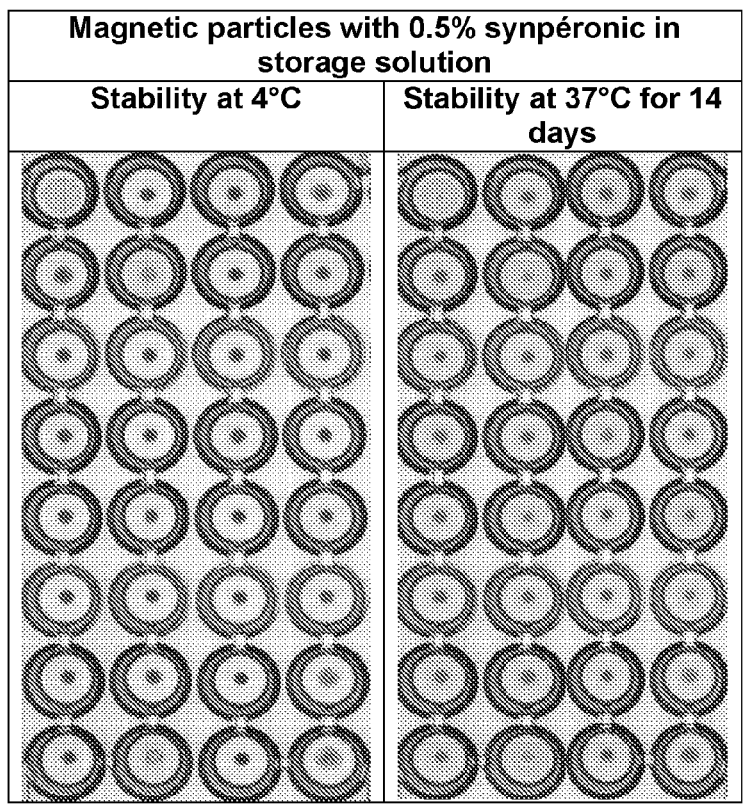
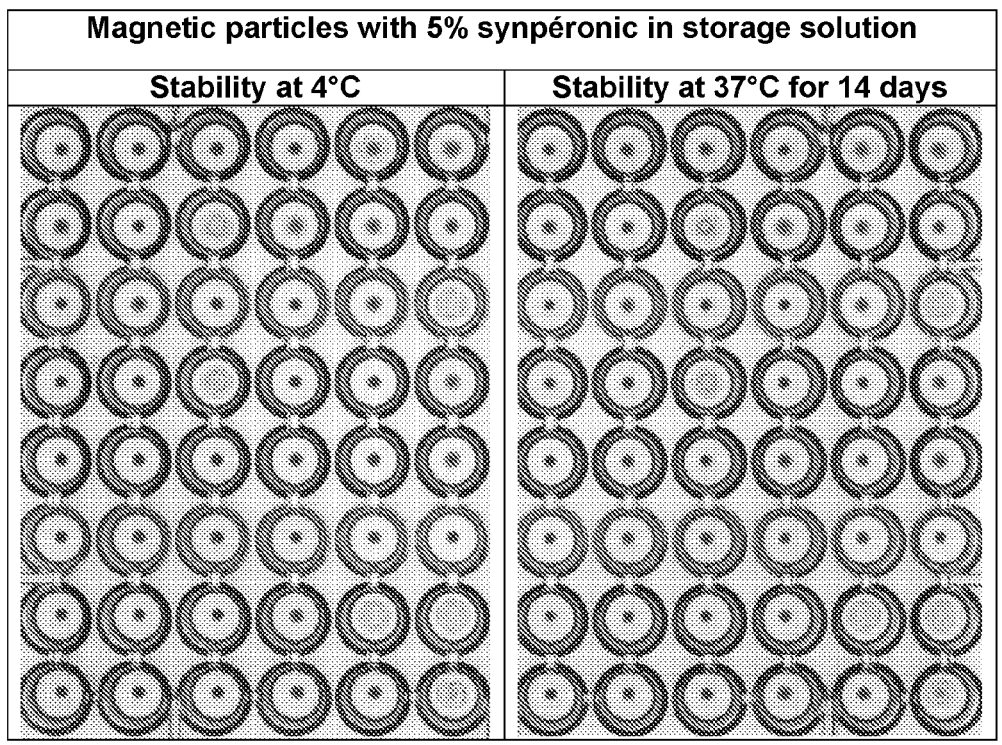
FIGURE 18

MAGNETIC IMMUNODIAGNOSTIC METHODS AND KIT FOR THE DEMONSTRATION OF ANTIBODY/ANTIGEN COMPLEXES IN ERYTHROCYTE BLOOD GROUPING AND PHENOTYPING

CROSS REFERENCE TO RELATED APPLICATIONS

This application is the National Phase of PCT/EP2011/062560 filed on Jul. 21, 2011, which claims priority under 35 U.S.C. §119(e) to U.S. Provisional Application No. 61/409,393 filed on Nov. 2, 2010 and under 35 U.S.C. §119(a) to patent application Ser. No. 1055973 filed in France on Jul. 21, 2010, all of which are hereby expressly incorporated by reference into the present application.

The current invention relates to a magnetic immunodiagnostic method for the demonstration of antibody/antigen complexes. Such a method involves the research and/or identification of antibodies or antigens, preferably anti-antigen antibodies or antigens of a blood group. This method implements a suspension of magnetic particles coated with an antibody anti-glycophorin A that can recognize and specifically magnetize erythrocytes. The invention also includes a device and kit for carrying out one such method.

Nowadays, blood transfusion consists in an intravenous injection of concentrated red cell preparations (globular concentrates) obtained from donor blood.

The principal risk of blood transfusions is the possibility of bringing together an antibody and its erythrocyte antigen in the recipient's body (person receiving the transfusion). Erythrocyte membrane antigens, notably blood group (or system) antigens, are found at the surface of erythrocytes, also called red cells or red blood cells, which are capable of being recognized by the immune system and of triggering an immune response and a hemolysis. The consequences of such an immunological reaction may range from inefficient transfusion with no clinical sign, to a slight clinical reaction (anxiety, shivers), serious clinical reaction (shock, hemoglobinurea, renal failure) or dramatic clinical reaction (shock, disseminated intravascular hemolysis) resulting in death.

Donor red cells are said to be compatible with the recipient's blood if the recipient has no circulating antibodies directed against the donor's erythrocyte antigens. Among all the antigenic variants of an erythrocyte membrane antigen constituting blood groups, over twenty erythrocyte antigen systems have been identified in humans to date: the ABO system with A, B and H antigens, the Rhesus system with D, E or e and C or c antigens, the Kell system with K or k antigens, the Duffy system (Fya, Fyb), the Kidd system (Jka, Jkb), the MNS system or other systems less frequently investigated in practice which also exist such as Lutheran Lewis, etc. . . .
Individuals with the same combination of erythrocyte antigens belong to the same erythrocyte blood group. Blood groups become even more complex and numerous when several antigen systems are used.

Except for pathological conditions, in the case of an autoimmune disease for example, an individual's serum can contain two types of antibodies directed against erythrocyte antigens:

a/ so-called regular antibodies directed against antigens of the ABO system (for example anti-A antibodies in group B individuals). These are IgM type immunoglobulins, capable of agglutinating red cells in vitro. This phenomenon is used to determine an individual's ABO group by means of the Beth-Vincent and Simonin tests (respectively forward and reverse grouping tests). The Beth-Vincent test makes possible to determine which antigens are carried by red cells (antigen phenotype) and the Simonin test makes possible to carry out a complementary study, in other words to detect anti-A and/or anti-B antibodies circulating in an individual's serum. In the Beth-Vincent test, an individual's red cells are brought into contact with test sera, or test antibodies. Each of them has a precise specificity, directed against an antigen of the ABO system. This is therefore a red blood cell agglutination test with test sera. In the Simonin test, also called reverse test, an individual's serum or plasma, containing the latter's circulating antibodies, is brought into contact with test red blood cells, or test erythrocytes. Each of them belongs to a specific antigen group of the ABO system. This is therefore a serum agglutination test with test red blood cells, b/ so-called irregular (or immune) antibodies whose presence in the serum of plasma is optional and which are directed against antigens of non-ABO systems. These are most commonly IgG isotype antibodies, which appear when foreign red cells induce antigenic stimulation. That's the case for example when following immunization against one or more antigens during a blood transfusion, or even during pregnancy due to a maternal immune reaction against foetal erythrocyte antigens different from to the mother's blood group, notably during birth.

The screening of these irregular antibodies is called irregular agglutinin test (IAT). This test is used to detect the presence or the absence of IgG directed against various erythrocyte antigens, in an individual's blood. For this, the test aims at demonstrating the binding of these antibodies on test red blood cells, whose antigens are known. This method is carried out simultaneously on many types of red blood cells and the comparison of the results makes possible to identify the specificity of the IgG present.

The risk is greater for the most immunogenic antigens, such as rhesus D, but also for other rhesus types (E>c>e>C), the antigen of the Kell system (K), the antigens of the Duffy system (Fy a, Fy b), the antigens of the Kidd system (Jka, Jkb), etc. . . .

In practice, it is not possible to take into consideration all these antigens when carrying out a transfusion, as obtaining the right blood group at the right moment would not be possible, especially as some antigenic combinations are extremely rare. Standard transfusions only take into account the ABO group plus rhesus D (Rh+ or Rh−). In situations when there is a risk of an irregular agglutinin, a number of other systems are taken into consideration, notably rhesus C and E and Kell, and at times other systems. Therefore, for these risk situations, it is important to ensure the compatibility between the donor's blood group and the recipient's blood group by taking into account the presence or risk of occurrence of these irregular agglutinins.

Thus, in recipient patients with irregular anti-erythrocyte antibodies or in a risk situation, such as patients receiving multiple transfusions but not having anti-erythrocyte irregular antibodies and in pregnant women, it is of importance to select erythrocyte concentrate units which are transfused in such a way that the donor's red cells are devoid of antigens against which the recipient's antibodies are directed or likely to appear.

This compatibility test is compulsory in these patients and is used preventively in all recipients prior to administration of erythrocyte concentrates by means of a direct compatibility test with the donor's red blood cells in the presence of recipient serum or plasma. Neither agglutination reaction and/nor lysis reaction in the techniques used in IAT should be found.

In clinical transfusion practice, the erythrocyte phenotype, which corresponds to research and identification of the antigens of the blood group at the surface of red blood cells (with the exception of the ABO system in which the presence of the corresponding regular antibodies is also researched), concerns both the recipient and donor.

For the recipient and donor, three levels of erythrocyte phenotype exist in order to provide the recipient with compatible erythrocyte concentrates as a function of risk situations:
- determination of ABO group (or ABO group) and standard rhesus (presence or absence of antigen D),
- determination of Kell and rhesus phenotype (presence or absence of antigen C, E, c, e and K), and
- determination of extended (or larger) phenotypes (presence or absence of antigens of the Duffy system (Fya and Fyb), the Kidd system (Jka and Jkb) and of the MNSs system (antigens S and s), other antigens could be possibly researched depending on the type of risk and/or irregular antibodies found in the recipient's serum.

The techniques normally used for phenotyping consist, in general, in screening for the presence or absence of the antigen being investigated, using test sera containing the appropriate antibodies. Preferably, these antibodies contained in these test sera are agglutinating in nature (IgM or IgA), thereby enabling to obtain total or partial agglutination of the erythrocytes to be phenotype when these latters carry the antigen corresponding to the antibody present in the serum. Nevertheless, it is possible to use non-agglutinating test antibodies (of IgG type), in which agglutination is triggered by an anti-immunoglobulin and becomes visible after a centrifugation step and resuspension of the residue obtained (known as the Coombs indirect technique). It is also possible to use non-agglutinant test antibodies where the presence of these test antibodies bound to the red cells is visualized by means of an anti-immunoglobulin bound to a solid phase (immuno-adhesion technique). Results are read with the naked eye or by means of an appropriate device.

For research or identification, in a sample of the patient serum or plasma to be tested, of blood group anti-antigen antibodies, regular for the ABO or irregular for IAT, the patient's plasma or serum is brought into contact with erythrocytes (also called red blood cells or test red blood cells), of known antigenicity for a number of blood group systems (ABO, Rhesus, Kell, Duffy, Kidd, MNSs, etc.).

In the case of IAT, for which the antibodies likely to be present are more likely to be non-agglutinant, the used technique is indirect Coombs by agglutination using anti-immunoglobulin or by immuno-adhesion to a solid phase coated with an anti-immunoglobulin For IAT, a first step involves the use of a panel of red cells, this is called screening (two or three red cells from different groups selected so as to include the maximum number of antigens of importance in transfusion) and makes it possible to detect (but not to identify) the presence or absence of irregular antibodies. When screening is positive, identification of the specificity of the irregular antibodies present is carried out by means of a panel of red cells, called identification red cells, and including 10 to 15 or even 20 different phenotyped red blood cells in the vast majority of known blood group systems.

In the case of compatibility test (also called cross match), the donor red blood cells originating from blood bags that may be transfused, are brought into contact with the patient's serum or plasma. Usually a centrifugation step is performed to observe agglutination due to the presence of antibodies in the patient's serum and reactive with donor red cells (ABO incompatibility or irregular antibodies of IgM or IgA type). If this first step is negative, it is followed by a search for irregular antibodies using an anti-immunoglobulin (indirect Coombs technique).

There are numerous variants of the techniques used for phenotyping or IAT in the blood transfusion field. These techniques may be manual, on an opaline plate, in a tube or in a microplate well, or in gel column or completely automated by means of a robot for dispensing sample and reagent, shaker, incubator, centrifuge and automatic reader, the programmes of which are suitable for the techniques implemented.

The used techniques include techniques where the presence of anti-antigen antibodies of the blood group or antigens of the blood group is based on demonstration of agglutination of red cells after centrifugation, using a transparent mini-filtration column (Sephadex® gel or microbeads) where the opening at the upper end acts as an incubation chamber, and for which the cut-off threshold selected for the column prevents agglutinated red cells after centrifugation from passing through the column (see in particular patent EP 0 194 212 or patent EP 0 755 719).

We can also cite techniques where phenotyping or IAT is based on demonstration of red cells sensitised with an antibody after centrifugation, followed by immunoadhesion using a separation barrier consisting of a gel or liquid whose density is selected such that only red cells can cross this barrier during centrifugation, with the reaction container being coated in the lower area with an anti-immunoglobulin in order to trap sensitised red cells and give a characteristic image (EP 0 058 780, WO 98/02752).

Among the variants of the techniques used for phenotyping or IAT, we can also cite those which have been generally developed to research, in a sample, an analyte capable of binding to a cell using magnetic particles, this in particular in order to eliminate centrifugation, a process required in agglutination-based techniques such as the anti-globulin technique (Coombs indirect method by agglutination or immunoadhesion to a solid phase) for IAT or phenotyping. This is also the case, as for IAT, when it is necessary to wash sensitised red cells in order to eliminate non-specific antibodies capable of recognising the anti-immunoglobulin used in the subsequent step.

The centrifugation step is in fact always difficult to carry out in methods that are to be fully automated, notably dun to the cost and cumbersome nature of centrifuges, their handling, etc.

Magnetic particles have been used for many years for the detection of complexes of the ligand-receptor or antibody-antigen type. We can cite the methods described in the following patent documents WO 92/17781, EP 0 426 170, EP 0 351 857 EP, 0 528 708 or EP 0 230 768.

Thus, it would be useful to have available a quick and simple method for the detection of the presence of an antibody specifically directed against a given antigen in a complex reaction mixture containing antibodies directed against other antigens, in which method there is neither a washing step nor a centrifugation step. Such a method without a centrifugation step and without a washing step, notably for IAT and for phenotyping, presents the advantage of being usable on a practical and available support, such as a microplate, of being fully automated.

This is precisely the object of the invention

The present invention consists on the improvement of the patent WO 2007/051844, in that it combines the specific magnetization of the red blood cells through magnetic beads coupled to an antibody specific for erythrocyte antigen and a test method without washing step, using an anti-immunoglobulin coated to the bottom of wells of a microplate. This is a so-called immuno-adherence method.

This method combines a viscous solution, which serves as a barrier filter to free antibody unbound to red blood cells, and a diluent deposited on the filter barrier containing magnetic beads coupled to an antibody specific for an erythrocyte antigen.

In the other hand, the present invention allows also, the magnetization of red blood cells of donor or patient in grouping and phenotyping tests by direct agglutination method. In these cases, the magnetization of red blood cells replaces the centrifugation steps enhancing the agglutination.

In all cases, during the incubation of the red blood cells with the serum of the patient or donor, or with the serum tests (in case of grouping or phenotyping) the cells will be magnetized by a specific antibody. This magnetization can magnetize any red blood cell derived from any solution or buffer and can eliminate all disturbing elements present in the serum during the magnetization.

The principle of the invention is to magnetize specifically the red blood cells to make them moving under the influence of a magnetic field, and thus be able to perform all the steps necessary to implement testing of immuno-hematology.

The invention relates to the method of a specific magnetization of red blood cells and also to their use in a kit for the tests of blood grouping, phenotyping, including the Simonin test, antibody detection tests in IAT, the compatibility test between donor and recipient, and in the direct antiglobulin test.

The specific magnetization of red blood cells consists in the binding of magnetic particles to red blood cells using a monoclonal or polyclonal specific antibody for a blood group antigen expressed on the membrane of red blood cells. This specific antibody for blood group antigen is itself covalently fixed to functionalized magnetic particles.

The choice of the targeted antigen, recognized by the antibody-coupled magnetic beads, was made on a transmembrane protein highly expressed on the surface of human red blood cells. This transmembrane protein is expressed without any ethnic distinction and is not present in soluble form in human plasma. Thus, the transmembrane protein chosen as the targeted antigen is the glycophorin A.

Glycophorin A (GPA) is the most abundant red cell sialoglycoprotein and is present on all red blood cells of all ethnic groups. No soluble form of this glycoprotein exists in the human plasma. The number of copies of glycophorin A per red cell has been estimated at $1 \times 10^6$.

GPA consists of a polypeptide chain of 131 amino acids (mature chain), organized into three domains: an extracellular N-terminal domain of 72 amino acids, a hydrophobic membrane spanning domain of 23 amino acids and a C-terminal cytoplasmic domain of 36 amino acids.

The extracellular domain of this glycoprotein contains a highly proportion of serine and threonine residues and is heavily glycosylated with about 15-Oglycans and a single N-glycan.

The glycophorin A is known to carry the M and N antigens of the MNS system. These two antigens differ by a nucleotide polymorphism that leads to a change in the polypeptide chain of two amino acids: the first in position 1 and the second in position 5 of the polypeptide chain. This induces for an individual positive for M antigen by the presence of both a serine in position 1 and a glycine at position 5 on the polypeptide chain. On the other hand, an individual expressing the N antigen will present an amino acid leucine at position 1 and a glutamic acid at position 5 of the polypeptide chain.

These two antigens are located near the N-terminus of the protein of interest. Thus the used monoclonal antibody must have its recognition epitope in the extracellular portion of the sialoglycoprotein but also from a distance of the 2 antigens M and N.

Amino Acid Sequence of the Full Human GPA Protein (one letter code)

(GenBank Accession Number AAA88051)

```
mygkiifvll lsaivsisas sttgvamhts tsssvtksyi ssqtndthkr dtyaatprah evseisvrtv yppeeetger vqlahhfsep eitliifgvm agvigtilli sygirrlikk spsdvkplps pdtdvplssv eienpetsdq
```

The fragment AA 1-19 corresponds to the signal peptide sequence and the fragment 20-150 (131 amino acids length, in bold) to the mature chain In a preferred embodiment, the monoclonal antibody directed against glycophorin A (anti-GPA), selected to be coupled to magnetic beads, is a murine immunoglobulin of IgG isotype. This antibody was developed after immunization of mice with A1 human red blood cells. It is preferred to be directed against amino acids 38-44 of glycophorin A (mature chain, as above identified or natural variant thereof).

This monoclonal antibody is thus coupled covalently with superparamagnetic beads. So the monoclonal antibody anti-GPA, attached to magnetic beads, may recognize the antigen on the surface of erythrocytes and then cells are magnetized through the anti-GPA.

These red blood cells, sensitized by the magnetic particles coupled with an anti-erythrocyte antibody, are attracted by a magnetic field as well as they have blood antigens (group and phenotype) on their surface. They could then be used as a reactive support and moving vector for the antigen-antibody complex in an immunologic analysis test (FIG. 1).

Other methods enabling the magnetization of patient's red cells by means of ferromagnetic particles are already known.

The WO 2005/121805 patent describes the use of very small-sized ferromagnetic particles for red cells magnetization and their use in grouping and phenotyping tests and for the detection of irregular antibodies (IAT tests). The red cells magnetization is made on a non specific way by means of a direct contact between the red cells and the ferromagnetic particles. Such a method enables to move the patient's red cells under the influence of a magnetic field.

The patent document EP 0 230 768 also describes a co-aggregation method for magnetic particles capable of binding to a substance contained in a sample by means of polycationic and polyanionic compounds in the presence of a magnetic field. In particular, this document describes the separation of plasma in a sample of whole blood containing red cells in which the method involves sequential addition to a container placed on a magnet of the whole blood sample and a ferrofluide (FeCl2/FeCl3) coated with succinylated bovine serum albumin, aggregates of the erythrocytes particles obtained in this way are then drawn towards the magnet, thus making it possible to collect plasma clarified by decantation.

The WO 02/46758 patent describes a method for red cells magnetization by means of magnetic particles beforehand activated by bovine serum albumin so that to create numerous non specific and low intensity interactions between the red blood cell surface and the particles.

These techniques using magnetic beads or modified ferrofluids for magnetize red cells enable to eliminate the centrifugation steps. Nevertheless, they have the disadvantage of implementing non-specific interactions between the magnetic particles and the red cells, but also non-specific interactions between these magnetic particles and all the elements present in the biological solution. Those non-specific interactions between magnetic particles and red cells can be modified by any other present element and notably by the plasma elements from the patient to be tested when there is a contact between the magnetic particles and the erythrocytes.

The current invention has the advantage of bind specifically the magnetic beads on red cells by means of specific recognition of an antigen exclusively present on the surface of these erythrocytes. This method enables to magnetize the red cells in any conditions, without being hindered by the protein and/or glucidic elements present in the medium during the magnetization reaction.

Many magnetization methods are already known in which magnetic particles are bound to markers by means of covalent or specific interactions.

Currently, very numerous diagnostic systems are based on the use of functionalized magnetic particles. They are either used for the research of antibodies present in the biological medium or for the research of antigenic structures inducing an immune response from the host.

That is the case for the ELISA systems, for example. In such systems, the functionalized magnetic beads are indeed coupled with antigens or antibodies and are used as reactive support for the analyte detection in plasma. The magnetic supports enable to carry out washing steps while eliminating over the centrifugation steps.

Or else, the beads coupled to antibodies are used to sort a cell population expressing the CD4 antigen in a sample of human blood; it can be possible to bind specifically a ferromagnetic particle on the surface of CD4 positive cells by means of an appropriate antibody. Then the whole blood is submitted to a magnetic field to isolate the population of cells that interacts with magnetic particles.

As for the current invention, the magnetized erythrocytes (also called magnetized red blood cells) are used as a support for detection of irregular antibodies (IAT), for cross-matching test or for direct antiglobulin test (DAT). It has to be noted that this magnetization process neither mask the antigens present on the surface of the red cell, nor interfere with the detection of irregular antibodies directed against erythrocyte antigens.

The current invention consists in magnetizing the red blood cells in a specific way but also in using directly those specific beads in the reactive medium.

For example, for the detection of irregular antibodies test, several approaches can be used to carry out this test by means of beads coupled with anti-glycophorin A (anti-GPA).

Thus, in a first embodiment, the object of the invention is a method for the magnetization of erythrocytes, wherein it consists of the following steps:
 a) the coupling of antibody anti-GPA on the surface of the magnetic particles, and,
 b) the contact of magnetic particles coated with anti-GPA obtained step a) with erythrocytes.

Preferably, the coupling of the antibody is performed by passive adsorption, by covalent coupling, or by ionic hydrogen binding, or by coupling type ligand/receptor (eg avidin-streptavidin), this according to the nature and functionalization of magnetic particles used.

The immunodiagnostic techniques, for capture or for cellular sorting, involving magnetic particles have been the subject of many publications and are well-known to the man skilled in the art.

Among these techniques, we can cite those using a functionalization of a magnetic particle, thus making it possible to obtain a reactive group on the surface capable of reacting, under appropriate conditions and with the suitable reagents, with the antigens that are to be grafted covalently to the particle, notably an acid group, amine group, epoxy or aldehyde group to cite the most common.

We can also cite those techniques making use of passive adsorption of the antigen that has to be bound to the particle, notably by adequate treatment allowing to get positively or negatively charged beads, depending on the antigen and conditions under which this passive adsorption has to be carried out.

Preferably still, the anti-GPA antibody is a mammal antibody, preferably from murine or human origin, and capable of specifically recognize the glycophorin A expressed by erythrocytes, preferably directed against the sialoglycoprotein glycophorin A, preferably again against its extra-membranous domain.

Still more preferably, a monoclonal antibody anti-GPA directed against an epitope from the extra-cellular part of the sialoglycoprotein glycophorin A, the said epitope bearing neither part nor the totality of the M or N antigen, notably the said epitope not containing the fragment of amino-acids of 1-5 from the N-terminal part of the glycophorin A.

Preferably, the said method of magnetization of erythrocytes, according to the invention, is characterized in that it further comprises a step in which the suspension of <<magnetized>> erythrocytes obtained in step b) is diluted in a diluent containing a non-ionic detergent as defined in the method below, the said diluent being preferably a diluent of low ionic strength containing an hydrophilic polymer as also defined below.

In a preferred embodiment, the present invention is a method for the demonstration of a specific complex formed by reacting an anti-antigen antibody, coing from blood group or phenotype, which is present in a solution and an antigen from blood group or phenotype and which is expressed by erythrocyte, the said erythrocyte bound to a magnetic particle, the reaction taking place in reactor with an open top and sealed base whose diameter decreases at least in the area close to the base in such a way that it forms an inclined wall being at least partially coated with an anti-immunoglobulin or with any other compound capable of binding to the antibody of the said formed complex, the said method consisting into several steps:
 a) prior to the contact between the magnetic particles suspension bearing the erythrocytes and the solution likely to contain anti-antigen antibodies from blood group or phenotype:
   filling up of the reactor with a viscous solution such that to cover up at least part of the inclined wall of the reactor,
 b) contacting the solution containing or likely to contain said antibody with the magnetic particle suspension carrying or likely to carry said antigen at a point above the viscous solution in the reactor, c) incubation of the reactor for a given time required for complex formation between the magnetic particles bearing the erythrocytes and the anti-antigen antibodies of blood group or phenotype likely to be contained in the solution and to recognize specifically the said antigens of blood group or phenotype carried by the erythrocytes;

d) application of a magnetic field to the said reactor and the stirring of this reactor, so that the magnetic particles being drawn towards the bottom and/or the inclined wall of the reactor; and e) reading with a naked eye and/or by any other suitable reading system of the image obtained at the bottom of the reactor and/or inclined wall of the reactor coated with the said anti-immunoglobulin or with any other compound capable of binding to the antibody, the image obtained making it possible to demonstrate the presence or not of a specific antibody/anti-antigen complex of blood group or phenotype, characterized in that the said magnetic particles bearing the erythrocytes are magnetic particles which have previously been coated with an antibody anti-glycophorin A (anti-GPA) and also in that the said erythrocyte is bound to the said magnetic particle by an antibody/antigen interaction.

In general, the antibody of the specific complex antibody/antigen can be from IgG, IgM, IgA or IgE nature or from any other class of antibodies.

The term "anti-immunoglobulin capable of binding to the antibody of said formed complex" refers here to anti-immunoglobulins, polyclonal or monoclonal, capable of recognising and binding any antibody, particularly human, whether IgG, IgM, IgA, or IgE (total anti-immunoglobulin), or certain specific categories of antibody, notably specific anti-IgG antibodies. Such anti-immunoglobulins, particularly human, are well known to the man skilled in the art and are available from many suppliers and will therefore not be described in detail here, especially in terms of their manufacturing processes.

Still preferably, when this antibody is of the IgG type, an anti-IgG is the preferred anti-immunoglobulin, notably human anti-IgG (directed against antibodies of human origin).

Still preferably, when this antibody is of the IgG or IgM type, a combination of anti-IgG and anti-IgM is preferred; notably from human origins.

The term "any other compound capable of binding to the antibody of said formed complex" refers in particular to protein A type compounds or protein G type compounds, well known to the man skilled in the art, for the recognition and specific binding of antibodies.

In a preferred embodiment, the present invention includes a method according to the invention, characterized in that the method used to magnetize the erythrocytes is the process of magnetization of erythrocytes according to the invention described above.

In a preferred embodiment, the present invention includes a method according to the invention, characterized in that prior contacting the suspension of magnetic particles bearing the erythrocytes with the solution likely to contain the anti-antigen antibodies of blood group or phenotype, the said suspension of magnetic particles bearing erythrocytes is in suspension in a diluent whose density is superior to 1 and inferior to the density of the said viscous solution.

In an equally preferred embodiment, the said process according to the present invention is characterized in that said steps a) and b) are the following:

a) Prior to bring into contact the suspension of magnetic particles bearing the erythrocytes and the solution likely to contain the anti-antigen antibodies of blood group or phenotype:
  i) preparation of the suspension of magnetic particles bearing the erythrocytes outside from the said reactor,
  ii) filling up of the reactor with a viscous substance so that to cover up at least partly the inclined wall of the reactor, then with the said diluent;

b) Bring into contact above the diluent the suspension of magnetic particles bearing the erythrocytes prepared during step a)i) and the solution containing or likely to contain the said antibody In another preferred embodiment, the said process according to the present invention is characterized in that the said steps a) and b) are the following:

a) Prior to the contact the suspension of magnetic particles bearing the erythrocytes and the solution likely to contain the anti-antigen antibodies of blood group or phenotype:
  filling up of the reactor with a viscous substance so that to cover up at least partly the inclined wall of the reactor, then with the said diluent then with the suspension of magnetic particles coated with anti-GPA then with the erythrocytes suspension;

b) Bring into contact in the reactor the solution containing or likely to contain the said antibody and the suspension of magnetic particles bearing the erythrocytes formed or under formation.

In another preferred embodiment, the said process according to the present invention is characterized in that the said steps a) and b) are the following:

a) Prior to the contact the suspension of magnetic particles bearing the erythrocytes and the solution likely to contain the anti-antigen antibodies of blood group or phenotype:
  i) preparation outside the said reactor of a suspension of magnetic particles coated with anti-GPA, the said magnetic particles being in suspension in the said diluent, or the availability of such a suspension already prepared,
  ii) filling up of the reactor with a viscous substance so that to at least partly cover up the inclined wall of the reactor, then with the suspension of magnetic particles coated with anti-GPA in the said diluent prepared in step a)i), then with the suspension of erythrocytes;

b) Bring into contact, in the reactor of the solution containing or likely to contain the said antibodies and the suspension of magnetic particles bearing the erythrocytes formed or under formation.

In this latter preferred embodiment, the said process according to the present invention is characterized in that:
  a) at the end of step a)i), a contact is established between the said suspension containing the magnetic particles in suspension in the said diluent with the erythrocytes suspension outside from the reactor to form a suspension of magnetic particles bearing the erythrocytes in suspension in the said diluent; and
  at the step a)ii) filling up of the reactor with a viscous substance so that to at least partly cover up the inclined wall of the reactor, then with the said suspension of magnetic particles bearing the erythrocytes in suspension in the said diluent;
  b) Bring into contact, in the reactor the solution containing or likely to contain the said antibodies and the suspension of magnetic particles bearing the erythrocytes.

In another particularly preferred embodiment, the present invention includes a method according to the invention, characterized in that in the context of automation, the dispensing of the reagents by a lab automate, the said steps a) and b) are the following:

a) Prior to bring into contact the suspension of magnetic particles bearing the erythrocytes and the solution containing or likely to contain the anti-antigen antibody of blood group or phenotype:

i) preparation outside the said reactor of a suspension of magnetic particles coated with anti-GPA, the said magnetic particles being in suspension in the said diluent, or the availability of such a suspension already prepared, ii) Filling up the reactor with the suspension of erythrocytes, then with a suspension of magnetic particles coated with anti-GPA in the said diluent prepared at the step a)i), then if necessary after stirring, with the said viscous substance so that to cover up at least partly the inclined wall of the reactor, the said viscous substance being injected at the bottom of the reactor;

b) Bring into contact in the reactor of the solution containing or likely to contain the said antibodies and the suspension of magnetic particles bearing the erythrocytes formed or under formation.

Figure 1B:
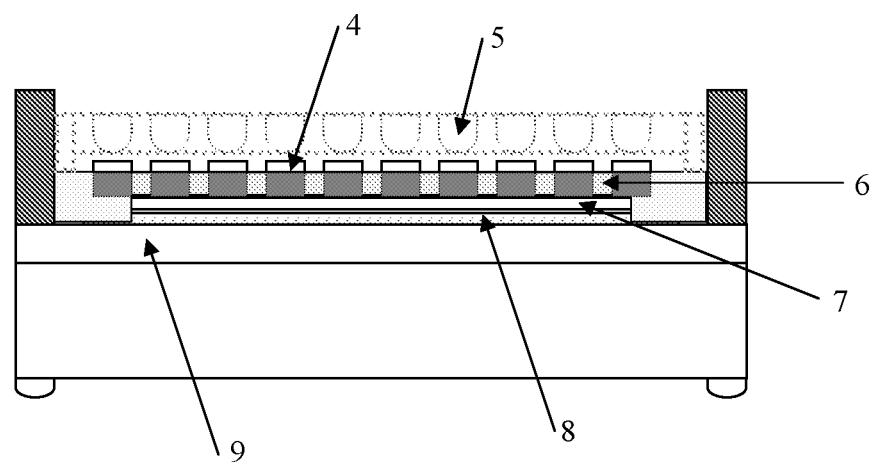

In a preferred embodiment, the present invention includes a method according to the invention, characterized in that at the step d), the application of a magnetic field to the said reactor and stirring of the reactor are carried out simultaneously (see FIGS. 1A and 1B as example of the device performing these different steps).

In preferred embodiment, the present invention includes method according to the invention, characterized in that in step d) the application of the magnetic field to the said reactor and the stirring of the reactor are carried out simultaneously (see FIGS. 1A and 1B as example of the device allowing to perform these different steps).

The term "simultaneously" refers here a period of time not exceeding more than 20 sec, where only the stirring or the application of the magnetic field is carried out.

In another preferred embodiment, the present invention includes a method according to the invention, characterized in that in step d) the application of the magnetic field and the stirring are carried out simultaneously during a period between 2.5 min and 10 min, preferably for a period between 5 min and 6 min.

In another preferred embodiment, the present invention includes a method according to the invention wherein in the step d) the application of the magnetic field is produced by a magnet located outside the reactor in such a way that the magnetic particles are attracted in the bottom of the reactor.

In another preferred embodiment, the present invention includes a method according to the invention, characterized in that in step d) stirring consists of rotary stirring.

In another preferred embodiment, the present invention includes a method according to the invention, characterized in that in step d) stirring is carried out at a rate between 250 and 750 rpm, preferably at 600 rpm.

In another preferred embodiment, the present invention includes a method according to the invention, characterized in that in step c), the incubation period is between 10 min. and 30 min. at a temperature between 20° C. and 40° C., preferably at a temperature of 37° C.±1° C.

In a particularly preferred embodiment, the present invention includes a method according to the invention, characterized in that in step d), the agitation of the reactor is performed in the presence of the magnetic field.

In step d), the magnetic field application step and reactor stirring step can be carried out starting with one or the other of the steps but in such a way that application of the magnetic field and stirring take place simultaneously for at least a given period of time.

Evidently, also included in the method according to the invention a variation of the method according to the invention in which application of the magnetic field is carried out prior to stirring of the reactor in step d) of the method, with application of the magnetic field alone (without stirring) not exceeding a period of two minutes at the most, preferably one minute 30 s, one minute, or 30 s. This is also the case when stirring is carried out prior to application of the magnetic field, whereby the stirring period alone does not exceed a duration of 2 minutes at the most, preferably 1 minute 30 s at the most, 1 min, or 30 s.

The present invention includes a method according to the invention wherein in step d), application of the magnetic field is carried out by means of a magnet located externally below the reactor such that the magnetic particles are drawn towards the base of the reactor, preferably along the longitudinal axis of the reactor.

In a preferred embodiment of the method of the invention, in step d) said magnet is a permanent magnet of magnitude ranging from 8000 to 16000 Gauss, preferably from 10000 to 14000 Gauss, more preferably still from 11500 to 12500 Gauss, with a magnitude of 12000 Gauss being the most preferred.

In a preferred embodiment, the present invention includes a method according to the invention wherein in step d) stirring is carried out by means of a rotary stirrer.

The term "rotary stirrer" refers here in particular to a rotary platform with an amalgamated reactor, or set of reactors in the case of a 96-cupule microplate (refer to FIGS. 1A and 1B).

In a particular mode of stirring, the present invention includes a method according to the invention wherein in step d), stirring consists of rotary stirring having an orbit in a proportion between 1.0 mm and 2.5 mm diameter, preferably between 1.25 and 2.25 mm, between 1.5 mm and 2 mm diameter, with 2 mm being the preferred orbit diameter when the reactor has a diameter of 7 mm at its widest point.

The term "proportion" signifies that, for example when the diameter of the widest section is double or half of 7 mm, the corresponding diameter of the rotation orbit mentioned will be doubled or divided by two.

The term "orbit for rotary type stirring" refers to the diameter of the circle described by the lowest point of the reactor in the course of the stirring process (lowest point of the reactor's longitudinal central axis).

In a preferred embodiment, the present invention includes a method according to the invention wherein in step d), stirring is carried out at a rate between 250 and 750 rpm, preferably between 400 and 600 rpm.

In a particular embodiment, the magnet located between each of the reactors forms part of the stirring platform (see also FIGS. 1A and 1B).

In the latter case, the longitudinal central axis of the magnet located under the reactor follows the orbit formed by the longitudinal central axis of the reactor during stirring.

In a particular embodiment, the magnet located under each of the reactors is not fixed to the stirring platform. In this case, the longitudinal central axis of the magnet located under the reactor does not move and does not follow the orbit formed by the longitudinal central axis of the reactor during stirring.

The present invention includes a method according to the invention wherein in step c), the duration of incubation is between 10 minutes and 30 minutes, preferably between 15 and 25 minutes.

In a preferred embodiment, the present invention includes a method according to the invention wherein in step c), incubation is carried out at a temperature between 10° C. and 40° C., preferably between 25° C. and 40° C., between 30° C. and 40° C., preferably around 37° C. (37° C.±1° C.).

In a preferred embodiment, the present invention includes a method according to the invention wherein in step b), incubation is carried out at a temperature between 30° C. and 40° C., preferably at 37° C.

In another preferred embodiment, the present invention includes a method according to the invention, characterized in that the magnetic particles have a diameter between 100 nm and 3.0 µm, preferably between 200 nm and 1.5 µm, preferably functionalized by a Tosyl group, a carboxyl group, an amine group or even an alcohol group.

In another preferred embodiment, the present invention includes a method according to the invention wherein the said magnetic particles contain at least in weight 40% of ferromagnetic compounds, preferably between 40% and 50%.

In a preferred embodiment, the present invention includes a method according to the invention, characterized in that at the step a), the preliminary filling up of the reactor with a viscous substance or a homogeneous gel is performed with a viscous substance whose the density is such that it prevents the migration of antibodies not forming complexes with the antigens bound to the magnetic particles towards the inclined wall and the bottom of the reactor coated with anti-immunoglobulin or other compound capable recognizing the antibody in the step d).

In a preferred embodiment, the present invention includes a method according to the invention wherein the said viscous solution has a density greater than 1. More preferably, the method of the present invention is characterized in that said viscous solution is selected from the gels, preferably selected from gels derived from dextran Sephadex™ and Sepharose™ beads whose diameter can vary from 20 nm to 300 nm, preferably superfine G100™ or Sepharose™ 4B or 6B, among the PVP (polyvinyl pyrrolidone), PVP-40 or PVP-60 or albumin solutions of 30%±10% or even gelatin.

In a preferred embodiment, the present invention includes a method according to the invention wherein in the first step, the gel is dextran or agarose (Sepharose™ (Pharmacia, Sweden), namely Sepharose™ 4B or 6B).

In an equally preferred embodiment, when said solution is of the gel type, this gel is prepared in the presence of bovine serum albumin in order to increase the density of the gel solution, preferably to final concentrations in the gel solution of 5% to 15% w/v, preferably 10%±2.5%.

In a preferred embodiment, the present invention includes a method according to the invention wherein in the first step, the viscous solution or gel is Sephadex™ (Pharmacia, Sweden, or Sigma-Aldrich), preferably G-10™, G-25™, G-50™, G-75™, G-100™, G-150™ or G-200™, where the diameter of the dextran beads can range from 20 nm to 300 nm. More preferably, Sephadex™ is superfine G-100™.

Even more preferably, gel concentration particularly that of Sephadex™ or Sepharose™, is between 1.5% and 6%, preferably between 2% and 5%, between 2.5% and 4%. A concentration of 3%±0.5% in w/v is the most preferred, notably for Sephadex™, in particular for superfine G-100™.

In a preferred embodiment, the present invention includes a method according to the invention wherein in the second step, the said solution containing or likely to contain the beads coupled with anti-glycophorin A is deposited on the viscous solution prior to depositing the suspension of erythrocytes carrying or likely to carry said antigen.

In another preferred embodiment, the present invention includes a method according to the invention, characterized in that at step b), the solution containing or likely to contain the said antibody is deposed before the suspension of erythrocytes when this latter is deposed after the viscous solution and after the said diluent.

In another preferred embodiment, the present invention includes a method according to the invention, characterized in that the diluent has a density inferior to the density of the viscous solution and superior than the density of the solution containing or likely to contain the said antibody.

In another preferred embodiment, the method of the present invention is characterized in that the diluent is a solution comprising a hydrophilic polymer at a concentration enabling to adjust its density to a density between that of plasma or serum and that of said solution viscous.

In another preferred embodiment, the present invention is characterized in that the said diluent is a solution containing an hydrophile polysaccharidic polymer, preferably Ficol™, notably Ficoll™ 400, with a concentration range from 1% to 2.5% (w/v), by preference 2%±0.3%.

In another preferred embodiment, the present invention, is characterized in that the reactor is a microplate cupule with a round-shaped or a V-shaped bottom.

In a preferred embodiment, the present invention includes a method according to the invention characterized in that the antibody solution is a human plasma or serum sample wherein the objective is to detect the presence of an antibody directed specifically against an antigen of blood group or phenotype, and wherein the anti-immunoglobulin is a human anti-immunoglobulin (HAG).

In a particularly preferred embodiment, the method of the present invention is a method for detection and identification of irregular antibodies (IAT) in a sample of serum or plasma, characterized in that comprising a step in which the erythrocytes carried by the magnetic beads are group O erythrocytes.

In another aspect, the present invention includes a method for blood grouping and/or phenotyping characterized in that it comprises the method of the present invention and wherein the solution likely to contain the anti-antigen antibodies of human group or phenotype is a serum test containing antibody of known blood group/phenotype specificity.

In a particular aspect of the present invention, in case of direct agglutination method, the present invention allows both group and phenotype typing of all the antigens present on the surface of red cells as soon as there is an available antibody.

Thus the following antigens can be identified by the present invention, those from the ABO system, (A antigen, B antigen, A and B antigens simultaneously expressed, the H antigen), the antigens from the Rhesus system (D, C, c, E, e antigens or Cw), the antigens from the Kell system (K or k), the antigens from the Duffy system (Fya and Fyb), the antigens from the Kidd system (Jka and Jkb), the antigens from the MNS system (M, N, S and s) or else of other antigens that are less commonly investigated but that also exists, such as those of the Lewis system, the Lutheran system, etc . . . .

For the grouping and/or phenotyping, we can use serums tests, including monoclonal antibodies, or polyclonal or recombinant antibodies, of known specificities able to recognize and to bind to the antigen on the erythrocyte against which it is directed.

The anti-antigen tests antibodies of blood group could be in liquid solution or in dried form in a microplate.

If the antibodies present in the serums tests are from IgM type, the test implemented, will be an agglutination reaction without the use of an anti-immunoglobulin (see examples 9-11).

In this case, the magnetic beads coupled to the anti-GPA, will be incubated with the red cells to be phenotyped and at the same that the antisera.

In another cases when the serum tests are from IgG type, it is possible to realize a reagent containing an anti-immunoglobulin anti-IgG saturated with IgG anti-erythrocyte of interest. In this case the anti-IgG may become agglutinating and result in an agglutination reaction (see Example: blood phenotyping with IgG and/or IgM antibodies in liquid form).

The present invention is thus directed to a method characterized in that said method comprises the steps of:

a) preparation a suspension of magnetic particles coated with anti-GPA, the said magnetic particles being in suspension in a diluent, or the availability of such a suspension already prepared, b) i) contacting the suspension of said magnetic particles coated with anti-GPA with a suspension of erythrocytes which are desired to determine the blood group and/or the phenotype,
   ii) bring into contact in a reactor the suspension of magnetic particles bearing the erythrocytes formed or under formation in step b) with a serum test containing antibody of known specificity,
   iii) agitation or stirring c) incubation of the reactor for a given time necessary to the formation of the complex between the magnetic particles bearing the erythrocytes and the serum test;

d) application of a magnetic field to the said reactor and stirring of the reactor, such that the magnetic particles are drawn towards the bottom and/or the inclined wall of the reactor; and e) reading with a naked eye and/or with any other appropriate reading system, of the image obtained at the bottom of the reactor and/or on the inclined wall of the reactor, this obtained image making it possible to demonstrate the presence or not of the formation of a specific complex antibody/antigen of human group or phenotype.

In a preferred embodiment, the present invention includes a method according to the invention wherein:
   in step d), a magnetic field to the said reactor is applied with a step of stirring, such that the magnetic particles are drawn towards the bottom of the reactor; and
   in step e), the reading with a naked eye and/or with any other appropriate reading system, of an agglutination reaction obtained or not at the bottom of the reactor, this specific agglutination demonstrating the presence the formation of a specific complex antibody/antigen of human group or phenotype.

In a preferred embodiment, the present invention includes a method according to the invention wherein in that in step b) ii) said serum test is in solution or in dried form.

In a preferred embodiment, the present invention includes a method according to the invention wherein in that the magnetic particles have a diameter between 100 nm and 3.0 μm, preferably between 200 nm and 1.5 μm.

In a preferred embodiment, the present invention includes a method according to the invention wherein in that the said magnetic particles contain at least 40% by weight of ferromagnetic compounds.

In a preferred embodiment, the present invention includes a method according to the invention wherein in that in step d), the application of a magnetic field is carried out by means of a magnet located externally below the reactor such that the magnetic particles are drawn towards the bottom of the reactor.

In a preferred embodiment, the present invention includes a method according to the invention wherein in that in step d) said magnet is a permanent magnet of magnitude ranging from 10,000 to 14,000 Gauss.

In a preferred embodiment, the present invention includes a method according to the invention wherein in that in step b) iii) or/and d), stirring is carried out by means of a rotary stirrer.

In a preferred embodiment, the present invention includes a method according to the invention wherein in that in step d), application of a magnetic field to the said reactor and the stirring of the reactor are carried out simultaneously.

In a preferred embodiment, the present invention includes a method according to the invention wherein in that in step b) iii), the application of the agitation (or stirring) is carried out for a period of 5 sec to 3 min, preferably for a period of 1 min. to 2 min.

In a preferred embodiment, the present invention includes a method according to the invention wherein in that in step b) iii), stirring is carried out at a speed ranging from 1000 to 1200 rpm, preferably at 1200 rpm between 10 sec.

In a preferred embodiment, the present invention includes a method according to the invention wherein in that in step d), stirring is carried out at a speed ranging from 500 to 800 rpm, preferably from 650 to 750 rpm, preferably at 700 rpm.

In a preferred embodiment, the present invention includes a method according to the invention wherein in that in step c), the duration of incubation is range from 2 min. to 30 min, preferably between 8 et 20 min, more preferably at a temperature between 20° C. and 40° C., preferably at room temperature or 37° C.

In a preferred embodiment, the present invention includes a method according to the invention wherein in that in step d), the duration of magnetization is range from 2 min 30 to 7 min, preferably 5 min, more preferably at a temperature between 20° C. and 40° C., preferably at room temperature.

In a preferred embodiment, the present invention includes a method according to the invention wherein in that after step d) and before step e), a sequence of agitation is implemented at a higher speed (between 800 and 1000 rpm for 1 to 2 min 30 sec) in order to suspend the non-agglutinated erythrocytes, optionally followed by a new step of stirring ("step of recollection") in order to assemble small dispersed agglutinates if present at a lower speed (between 350 to 550 rpm, for 1 min to 2 min).

In a preferred embodiment, the present invention includes a method according to the invention wherein when the serum test is of IgG type, an agglutinated reagent is preliminary carry out by mixing an anti-IgG-immunoglobulin solution with a concentrated solution of the IgG antibody serum test.

In a preferred embodiment, the method according to the present invention is characterized in that the reactor is a microplate cupule with a round-shaped or a V-shaped bottom.

In a preferred embodiment, the method according to the present invention is characterized in that the erythrocyte concentration in the suspension of magnetic particles carrying the erythrocytes is between 0.2% and 2.5%, preferably between 0.5% and 1.5%, preferably 1%±0.3%.

In a preferred embodiment, the method according to the present invention is characterized in that the concentration of magnetic particles is between 0.001% and 0.007%, preferably between 0.003% and 0.005%.

In a preferred embodiment, the method according to the present invention is characterized in that the anti-GPA antibody is a mammal antibody, preferably from murine or human origin, and capable to specifically recognize the human glycophorin A carried by the erythrocytes, preferably directed against the sialoglycoprotein glycophorin A, preferably against its extra-membranous domain.

In a preferred embodiment, the method according to the present invention is characterized in that the anti-GPA antibody is monoclonal antibody directed against an epitope from the extracellular part of the sialoglycoprotein glycophorin A, the said epitope bearing partly or not at all the antigen M or N, notably the said epitope not containing the fragment aa 1-5 N terminal of the glycophorin A.

In a preferred embodiment, the method according to the present invention is characterized in that the anti-GPA antibody is coupled to the magnetic particles in a concentration between 5 µg/mg and 25 µg/mg of magnetic particles, preferably from 20 µg/mg±3 µg/mg of magnetic particles.

In a preferred embodiment, the present invention includes a method according to the invention wherein, in order to improve and/or to increase the sensitivity and specificity of the tests, anti-GPA antibody is coupled to the magnetic particles in a concentration between 1 µg/mg and 5 µg/mg of magnetic particles, with a preference of 2.5 µg/mg±0.5 µg/mg of magnetic particles.

In a preferred embodiment, the method according to the present invention is characterized in that said suspension of magnetic particles is a suspension including a non ionic detergent, preferably Synperonic™ PE/F68, Tween™ (20, 40 or 80) with a concentration between 0.1% and 1% (w/v), preferably from 0.25% to 0.75% (m/v), or 0.5%±0.15%.

The present invention enables, also, to carry out blood grouping and/or phenotyping by using the technique of immunoadherence on solid phase, as described in the irregular antibodies detection tests (IAT) and in which the patient serum is replaced by serums tests of known specificities and the red blood cells sample groups are replaced by the red cells of the patient or of the donor to be grouped or phenotyped.

Antigens from various blood system could be group or phenotype depending of the anti-serum used, ie anti-D, anti-Fya, Anti-Fyb, Anti-Jka, antiJkb, anti-S, anti-s, or others anti-serum specific of other blood group antigens.

The principle of the immuno-adherence technique that enabling phenotyping, consists in magnetizing the red cells of the donor or of the patient with beads coupled with anti-GPA and sensitizing them with anti-serums of specific interests. The presence of an antigen will be revealed by the capture of the anti-serum bound on the red cells by an anti-immunoglobulin bound at the bottom of the well of a microplate.

The grouping and/or phenotyping of a patient or donor is carried out from a blood sample collected on tube with an anticoagulant of EDTA type, Citrate ou Heparine.

A globular suspension between 1% and 2%, preferably 1% is performed, in a tube or in the well of a plate with a round bottom, by diluting 10 µl of packed red cells in 1 ml of diluent containing the magnetic beads coupled with anti-GPA. The concentration of the beads in the diluent, made of a sugar-based polymer diluted in a low ionic strength buffer=Liss Ficoll, can vary from 0.002% to 0.006%, with a preference for 0.004%.

In parallel, in a well of a 96 round bottom microplate, coated with a specific anti-IgG antiglobulin or with a combination of antiglobulins (anti-IgG et anti-IgM), a viscous solution or a gel of higher density, is deposited and enables to create a barrier between the reaction medium containing the red blood cells of the patient or donor and the anti-serum. The globular suspension at 1% previously diluted in the solution containing the magnetic beads coupled with anti-GPA, is deposited above the viscous barrier. Then anti-serum of specific interest is added on the globular suspension.

The microplate is then incubated for 20 minutes at 37° C. During the incubation step, the anti-serums bind to the corresponding antigen present or not on the red blood cells. During this sensitizing phase of the red cells by the anti-serum, the red blood cells are also magnetized by the magnetic beads coupled with anti-GPA, present in the diluent. Each antibody being specific to an antigen, the binding of the first does not prevent the binding of the other. Thus the red blood cells from the patient or the donor bearing or not the red blood cell antigens could be magnetized by the anti-GPA beads as well as sensitized by the antibodies present in the anti-serum. At the end of the incubation step, the microplate is placed on a microplate stirrer equipped with a magnetic plate which perfectly fits under the wells of the microplate. Under the influence of the agitation and the magnetic field, the magnetized red blood cells by anti-GPA, bearing or not the antibodies of the anti-serum, will move through the viscous barrier and will bind or not to the antiglobulin fixed at the bottom of the well. A positive reaction will lead to the formation of a thin film of red blood cells at the bottom of the well, whereas a negative reaction will lead to the formation of a clear-cut red blood cell pellet at the bottom of the well.

In another preferred embodiment, the present invention includes a method according to the invention characterized in that the erythrocytes concentration in the suspension of magnetic particles bearing the erythrocytes is 0.2% to 2.5%, preferably between 0.5% and 1.5%, preferably between 1% to ±0.3%.

In another preferred embodiment, the present invention includes a method according to the invention characterized in that the concentration of magnetic particles in said suspension of magnetic particles bearing the erythrocytes is comprised between 0.02% and 0.2%, preferably between 0.01% and 0.009%, preferably 0.004% 0.001%.

In a preferred embodiment, the present invention includes a method according to the invention characterized in that the concentration of magnetic particles in said suspension of magnetic particles bearing the erythrocytes is 0.007%±0.001%.

In another particularly preferred embodiment, the present invention includes a method according to the invention characterized in that the anti-GPA antibody is a mammal antibody, preferably from murine or human origin, and able to specifically recognize the human glycophorin A carried by the erythrocytes, preferably directed against the sialoglycoprotein glycophorin A, preferably against its extra-membranous domain, preferably still a monoclonal antibody directed against an epitope from the extracellular part of the sialoglycoprotein glycophorin A, the said epitope bearing partly or not at all the M or N antigen, notably the said epitope not containing the aa1-5N-terminal fragment from the glycophorin A.

In another preferred embodiment, the present invention includes a method according to the invention characterized in that the anti-GPA antibody is coupled with magnetic particles with a concentration ranged between 5 µg/mg to 25 µg/mg of magnetic particles, preferably at a concentration of 20 µg/mg of magnetic particles.

In another particularly preferred embodiment, the present invention includes a method according to the invention characterized in that, in order to increase the sensitivity and specificity of the tests, the anti-GPA antibody is coupled to the magnetic particles in a concentration between 1 µg/mg and 5 µg/mg of magnetic particles, with a preference of 2.5 µg/mg±0.5µg/mg of magnetic particles.

In another preferred embodiment, the present invention includes a method according to the invention characterized in that the said suspension of magnetic particles is at a concentration of between 0.004% and 0.002% (w/v) and more preferably at a concentration of 0.007%±0.001%.The coupling of anti-GPA antibody is carried out on magnetic beads containing functional groups.

These functional groups can be from different types such as amino functions (—NH2) or alcoholic groups (—OH), carboxylic acid groups (—COOH) or Tosyl groups, all these functions are well-known by the man skilled at the art.

The interactions thus established between the antibody and the magnetic bead can be from electrostatic, hydrophobic or covalent natures.

The covalent binding of the antibody on the magnetic beads is carried out by means of functional groups at the surface of the beads.

Suppliers of magnetic microbeads (or particles) suitable for use within the scope of the present invention include in particular Ademtech (33600 Pessac, France), who supply magnetic particles with a diameter of around 100 to 500 nm which can be functionalised by an acid or amine, as well as protocols and reagents which make it possible to carry out the These magnetic particles consist of over 50% of a ferromagnetic core (such as iron oxide), with this core being coated with polystyrene. Other companies also include Bioclone Inc. (San Diego, Calif., U.S.A.) which supplies a whole range of functionalised magnetic beads. In addition, there is also Dynal Biotech GmbH (Hamburg, Germany) with its wide range of Dynabeads™, which offers in particular magnetic microbeads activated with streptavidine, Tosyl or a carboxylic acid group. Another company that can be cited is Merck Chimie SAS (94126 Fontenay-sous-Bois, France) which has the Estapor™ range of magnetic microbeads with different particle sizes (200 nm to 1,5 µm) based on polystyrene or divinylbenzene containing up to 50% ferrites and which can be functionalised or not, for example by an acid or amine group, or Tosyl group. These particles are prepared by a method using polymerisation of styrene in the presence of a ferromagnetic compound.

Finally, we can cite the company JSR Micro (Japan), who proposes different sizes of magnetic particles, from 1 µm to 3 µm functionalised with streptavidine or by carboxylic acid or Tosyl group. Magnetic beads from JSR are composed of a core particle coated with magnetic substance, which is covered by a monomer to encapsulate the magnetic substance. Among these proposed particles we will prefer hydrophobic beads of 1 µm size with about 48% of iron content and a rate of carboxylic functions of about 15 nm per mg of beads. These beads can be coupled by physical adsorption or by chemical coupling.

Preferably, the invention includes the use of superparamagnetic beads, preferably magnetic particles with size up between 200 nm and 1.5 µm, preferably hydrophobics and functionalised with carboxylic acid or Tosyl groups.

The iron average rate of the magnetic beads is about of 45% for carboxylic beads and of about 30% for Tosyl beads.

In the present description beads or particle has the same meaning for designating "magnetic particules".

The functionalization rate for functional groups is variable, for beads from Tosyl type the number of functions varies from 40 to 80 µeq/gr of beads, whereas as for beads with carboxylic groups, the number of functions can vary from 20 µeq/gr to 350 µeq/g of beads.

In this invention we prefer using magnetic beads from ESTAPOR™, from 200 to 300 nm sized, containing at least 40% of ferromagnetic compound, and a number of carboxylic functions of about 130 µeq per gram of beads, obtained under the reference M1-030/40. Or with the same supplier, we can use magnetic beads containing Tosyl functions ranging from 40 to 80 µeq/gram of beads, for a bead of about 1.2 µm of diameter and obtained under the reference R01-24.

Another alternative that will be preferred, for this invention is the use of magnetic beads from JSR Micro company of a 1 µm diameter, from hydrophobic type functionalized with carboxylic groups at a rate of 17 nmol/gramme od beads and obtained under the reference MB 100.

For functionalized beads with carboxylic acid groups, a physical adsorption will be preferred rather than a chemical coupling.

The beads are coupled with a purified murine monoclonal antibody, of IgG2a isotype, specific of the glycophorin A.

The concentration of the anti-glycophorin A antibody, coupled with the functionalized magnetic beads can vary from 5 µg/mg of beads to 25 µg/mg of beads, with a preference for a concentration of 20 µg/mg of beads. More preferably, in order to improve and/or to increase the sensitivity and specificity of the tests, anti-GPA antibody is coupled to the magnetic particles in a concentration between 1 µg/mg and 5 µg/mg of magnetic particles, with a preference of 2.5 µg/mg±0.5 µg/mg of magnetic particles.

At the end of the coupling, the solution containing the beads coupled with the anti-glycophorin A consists of PBS buffer with 0.1% (m/v) BSA as well as a non ionic detergent, as Synperonic™ PE/F68 type. The Synperonic™ PE/F68 is a non ionic hydrophilic surfactant also called poloxamer Synperonic™ F68 and available at Sigma Aldrich under the reference: 81 112. This polymer made of three blocs consists of a hydrophobic central part made of polyoxypropylene blocs, surrounded by 2 hydrophilic blocs of polyoxyethylene.

The use of a detergent is particularly preferred when nano- or microparticles are used, in order to avoid the spontaneous aggregation of these magnetic particles which can happen in particular conditions of pH, of ionic strength and temperature. It has been notably demonstrated that the changing surface of the particles by means of adsorption of non ionic amphiphilic macromolecules such as poloxamers contributes to the non-aggregation of the magnetic particles in solution.

Notably when particles are put in the solution in a buffer of high ionic strength, such as the PBS (Phosphate Buffered Saline), the nano/microparticles tend to lose their colloidal stability and to aggregate. The addition of a surfactant enables thus to ensure this colloidal stability and to avoid an aggregation of the particles in a buffer of high ionic strength.

There are several types of non ionic surfactant such as the Tween™ 20, 60, and 80 or the Synperonic™ PE/F68 or F127. In this invention we prefer using the Synperonic™ PE/F68.

To ensure an efficient action on the colloidal stability of the beads coupled with the different antibodies, the concentration of the Synperonic™ must be superior to 0.1% and inferior to 2.5%, which is the point of viability of the cells in presence of this concentration of surfactant. With a preference for a concentration of 0.5% (m/v).

In another particularly preferred embodiment, the present invention includes a method according to the invention characterized in that the said suspension of magnetic particles is a suspension containing a detergent, preferably non ionic, preferably chosen among the poloxamers, such as the Synperonic™ PE/F68, or chosen among the Tween™ (20, 40, 60 or 80), the said detergents being at a concentration of between 0.1% and 1% (w/v), with preference for 0.25% and 0.75% (w/v) or 0,5%±0,15%.

Once coupled, the beads are then stocked at a concentration of 1% (m/v) in a solution containing PBS (0.3M)+0.1% (w/v) of BSA+0.5 (w/v) of Synperonic™ PE/F68, this until their dilution in the final diluent.

In another particularly preferred embodiment, the present invention includes a method according to the invention characterized in that, in order to improve and/or to increase the stability of the magnetic particles coupled with the anti-GPA, the concentration of non ionic detergent is between 0.5% and 10% (w/v), with a preference for 5% (w/v) of non ionic detergent.

Then the beads are diluted into a concentration of 0.004% or, preferably 0.007%, in the final diluent which will be distribute on the viscous solution (also called barrier filtering or also called gel) above the AHG.

This final diluent in which are diluted the beads coupled with the anti-glycophorin A, is from a density superior to 1 and is preferably composed by a buffer of low ionic strength (or <<LISS>> or <<BFI>> buffer) and an hydrophilic polymer, preferably an hydrophilic polysaccharide, notably the Ficoll™ 400. The concentration of this polysaccharide, in the buffer of low ionic strength is preferably of 2%. The buffer of low ionic strength is well-known from the man skilled in the art in immunohematology, in that it facilitates and accelerates the reactions between the antibodies and the red blood cells.

This buffer can be made as appropriate in the presence of a final concentration of serum albumin (BSA) between 1.5% and 6% (w/v), which enables to get a certain viscosity to the medium and to control the speed of progression of the red blood cells towards the revealing part of the microplate. The disadvantage using a buffer containing albumin is its tendency to make foam.

Therefore, we prefer substitute it by a compound that does not present any foam. We chose Ficoll™ 400, a polymer of sugars that can be quite easily hydrated and which is particularly stable in solution. It is a synthetic product whose reproducibility is demonstrated, because of its use in many biological protocols of cell separation. Its density is thus reproducible; it is colourless and does not foam because of its structure which freely interacts with water. The used concentration enables to get a solution density equal to the one obtained albumin at 3%. It opposes a necessary and sufficient cushion to the red blood cells in progression. The diluent density containing 2% of Ficoll™ 400 is thus equal to 1.013 g/cm3.

Example of preferred composition for the diluent containing the magnetic particles:
For 1 liter:
$Na_2HPO_4$, $2H_2O$: 0.213 g
$NaH_2PO_4$, $2H_2O$: 0.240 g
NaCl: 1.788 g
Glycin: 18.05 g
Na Azid: 0.9 g
Ficoll 400: 20g
Osmolarity: 310+/−20 mOsm
pH: 6.75+/−0.1

In some applications, notably when this involves improving the sensitivity or the speed of reaction (however without increasing the non specificity of the test), a low ionic strength buffer ISB can be used, also called LISS buffer (LISS for Low Ionic Strength Solution).

The man skilled in the art will know that buffer ao saline solution refers before to buffers commonly used inn the field of cell biology, notably immunohematology, in order to prevent lysis of red blood cells, notably for IAT or phenotyping applications. Such buffers or solutions can be, for example, buffers at a physiological pH between 6.8 and 7.5 with the molarity of the buffers constituents being adjusted such that the final solution obtained is similar in terms of osmotic pressure to the molarity of an NaCl type solution at 9 per thousand (close to 0.15M NaCl). In particular, we can cite but without this being limiting PBS type phosphate buffer at pH 7.0-7.4, well known to the man skilled in the art.

The composition of ISB or LISS buffers will therefore not be described here as these buffers are well known in immunohematology for their ability to boost agglutination reactions. These buffers are available from suppliers of reagents for hematology (for example, we can cite but without this being limiting a LISS buffer having the following composition, 16 g/l glycine, 0.03 M NaCl and 0.015 M phosphate at pH 6.7).

In another preferred embodiment, the present invention is carried out to implement a compatibility test between donor and recipient, or to implement a Direct Coombs test.

In another aspect, the present invention relates to a kit formed for demonstration of a specific complex formed by reaction between an anti-antigen antibody of blood group or phenotype, present in the solution and an antigen of blood group or phenotype carried by the erythrocyte, notably to carry out an IAT or a compatibility test, or for blood grouping, such as Simonin or Beth-Vincent test, or phenotyping, characterized in that:

a) a reagent including a suspension of magnetic particles coated with anti-GPA, preferably as defined in one of the methods according to the invention;

In a preferred embodiment aspect, the present invention relates to a kit according to the present invention, characterized in that it further comprises:

b)—a reactor or a group of reactors with an open top and sealed base whose diameter decreases at least in the area close to the base in such a way that it forms an inclined wall being at least partially coated with an anti-immunoglobulin or with other compound capable of binding to the antibody of the said formed complex, a container containing a viscous solution, or if need be, each reactor being partly filled up with the said viscous substance, the said viscous substance being as defined in one of the methods according to the present invention; and c) or if need be, a container containing a diluent, the said diluent being a solution including an hydrophilic polymer, preferably of polysaccharidic nature, preferably Ficoll™, notably Ficoll™ 400, with a concentration ranged from 1% to 2.5% (m/v), preferably from 2%±0.3%, d) or if need be, at least a magnet or a group of magnets which can be placed externally below the reactor (s), coupled with the rotary stirrer.

In another preferred embodiment, the said kit of the present invention is characterized in that it contains a suspension of test erythrocytes of known phenotype on which will be coupled to said magnetic particles of the suspension, preferably the erythrocytes suspension is of O group, and with a concentration ranged from 0.2% to 2.5%, preferably ranged from 0.5% to 1.5%, preferably 1%±0.3%.

Still preferably, the invention concerns a kit according to the invention, characterized in that the viscous substance and if need be the magnetic particles or the suspension of magnetized erythrocytes, or if need be the characteristics of the magnet and of the rotary stirrer, has or have the characteristics as defined for the methods according to the invention with also the preferences specified for these viscous solutions or other compounds and elements.

In a preferred embodiment, the kit according to the present invention is characterized in that it contains a suspension of test erythrocytes of known phenotype to which the erythrocytes will be coupled with the said magnetic particles of the suspension, preferably the erythrocytes suspension is from O group, and has a concentration between 0.2% and 2.5%, preferably between 0.5% and 1.5%, preferably 1%±0.3%.

In a preferred embodiment, the kit according to the present invention is for blood grouping or phenotyping and characterized in that it further contains a serum test, in solution or in a dried form, of known specificity.

In the present explanation the words erythrocytes, red cell and red blood cell will be equally used to name the same blood cell.

Still preferably, the invention relates to a kit according to the invention, characterized in that the said reactor is a microplate cupule, preferably with a round-shaped bottom (hemispherical) or with a V-shaped bottom, the microplate consisting of 96 cupules being the most preferred.

The figures and headings below as well as the following examples are intended to illustrate the invention without limiting its extent in any way.

FIGURES

FIGS. 1A and 1B: diagram of the view from above (FIG. 1A) and view from the side (FIG. 1B) of the stirring platform (Teleshake™) consisting of a soft iron plate under the microplate under which the soft iron plate each magnet is fixed magnetically in the form of a stack under each of the microplate cupule.

(1) Plastic spacer making it possible to obtain good spacing between magnets; (2) Elements making it possible to wedge the microplate on Teleshake; (3) Teleshake wedge making it possible to wedge the microplate; (4) Stack magnets; (5) Microplate; (6) Plastic spacer; (7) Mild iron plate on which magnets are magnetically fixed; (8) Cardboard plate isolating Teleshake from the magnetic field of the magnet stack; (9) Teleshake rotary tray.

FIGS. 2A and 2B: Diagram of a round based (or U-shaped) reactor cupule after coating with anti-immunoglobulin on the inclined wall (partially) and the base of the cupule prior to addition of the viscous solution and various solutions and reagents (FIG. 2A). Diagram of a round based (or U-shaped) reactor cupule after coating with anti-immunoglobulin on the inclined wall (partially) and the base of the cupule after the addition of the viscous solution and erythrocyte suspension "magnetized" in the diluent, and the addition of plasma or serum to be tested (example among others) (FIG. 2B).

FIG. 3: Photograph showing an image of a positive immunoadhesion reaction with antigens carried by erythrocytes (formation of specific complex adhering to the inclined wall coated with anti-immunoglobulin) (figure at left) and photograph showing an image of a negative immunoadhesion reaction with antigens carried by the erythrocyte (no formation of specific complex) (figure at right).

FIG. 4: Irregular antibodies test (IAT) using the methodology no 3.

FIG. 5: Titration of CNRGS (French National Reference Centre for Blood Groups), anti-D with the irregular antibodies test.

FIGS. 6 and 7: Cross Match test (compatibility test) realised with O group blood donors FIG. 8: Coupling of the anti-glycophorin A (GPA) on the magnetic beads.

Figure 9:
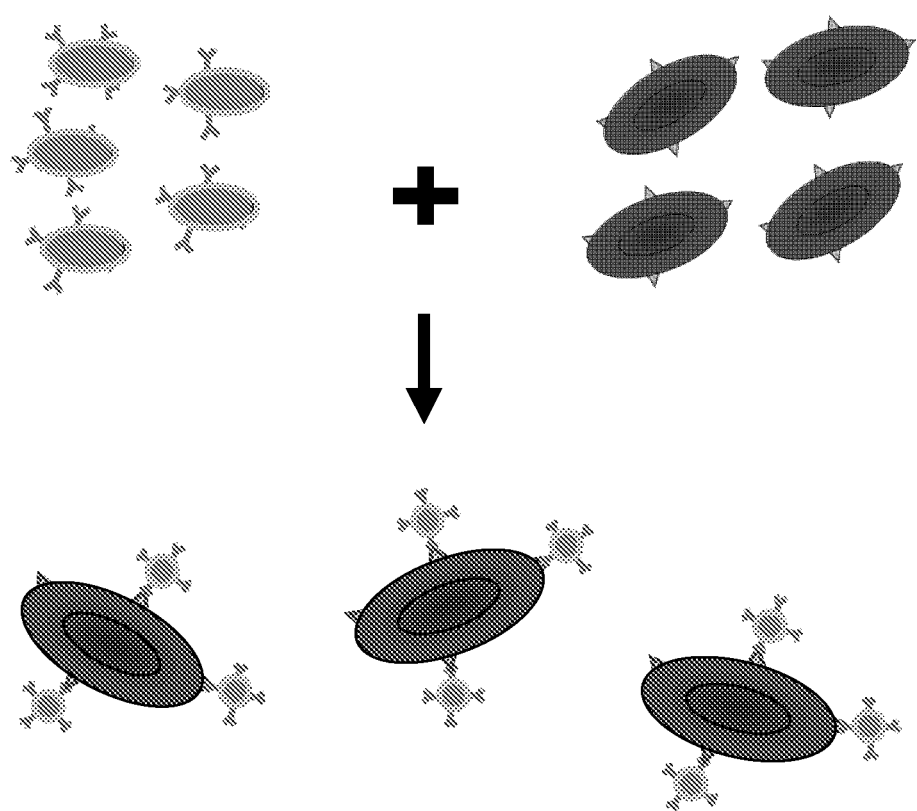
Figure 10:
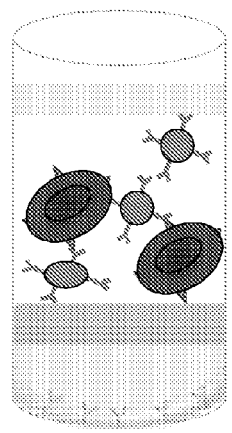
Figure 11:
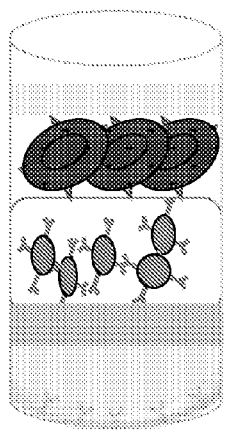
Figure 12:
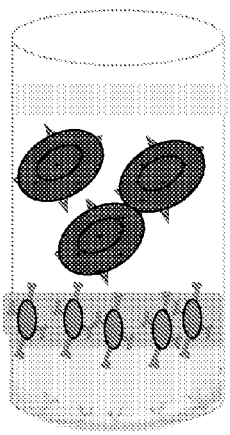

FIG. 9: Principle of magnetization of human red blood cells by anti-glycophorin A coated on magnetic particles FIGS. 10-12: Three methods of magnetization of erythrocytes with beads coupled to anti-GPA in the irregular antibodies test.

Figure 13:
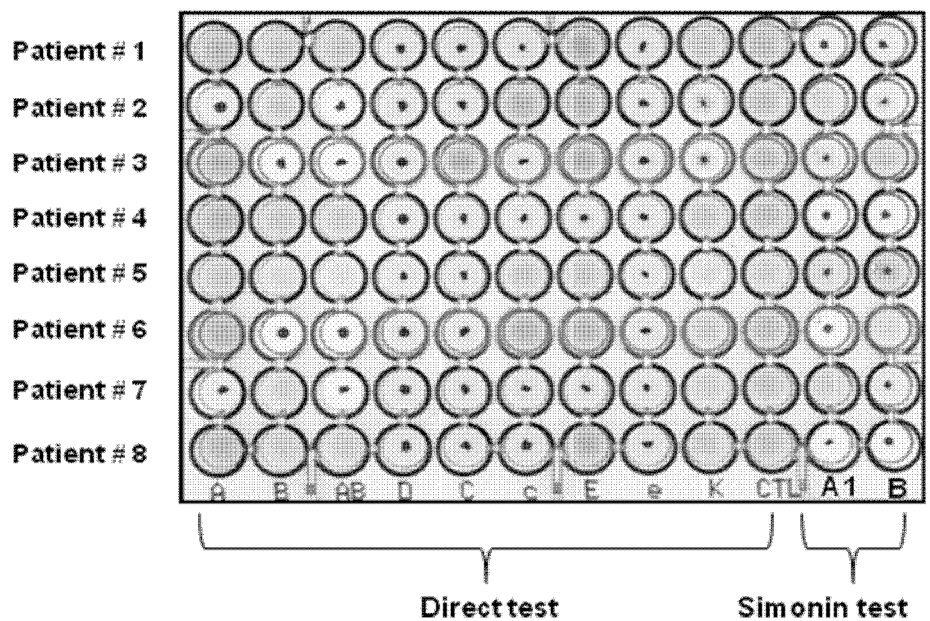

FIG. 13: Agglutination method for the grouping (including the Simonin test) and phenotyping of 8 patients.

Figure 14:
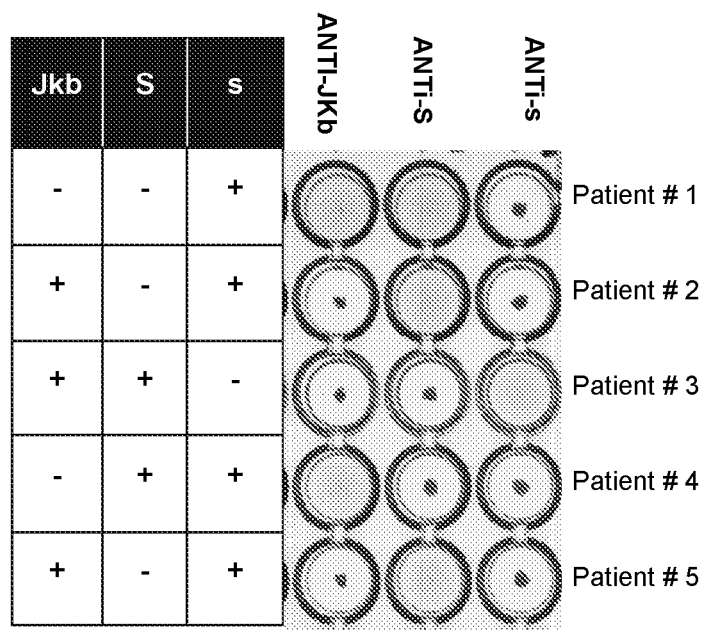

FIG. 14: Agglutination method for the extended phenotyping of 5 patients

Figure 15:
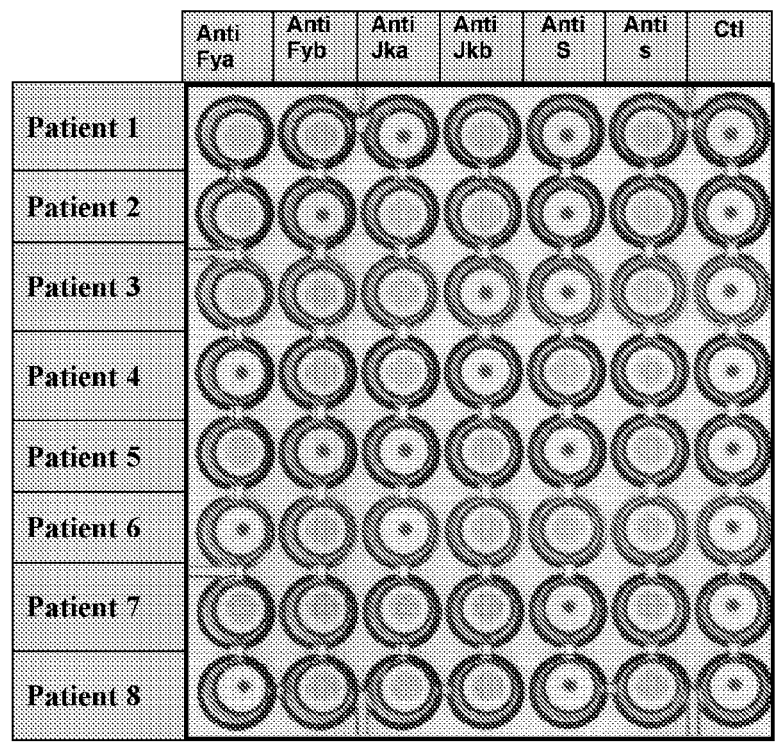

FIG. 15: Immunoadherence method for the extended phenotyping of 8 donors.

Figure 16:
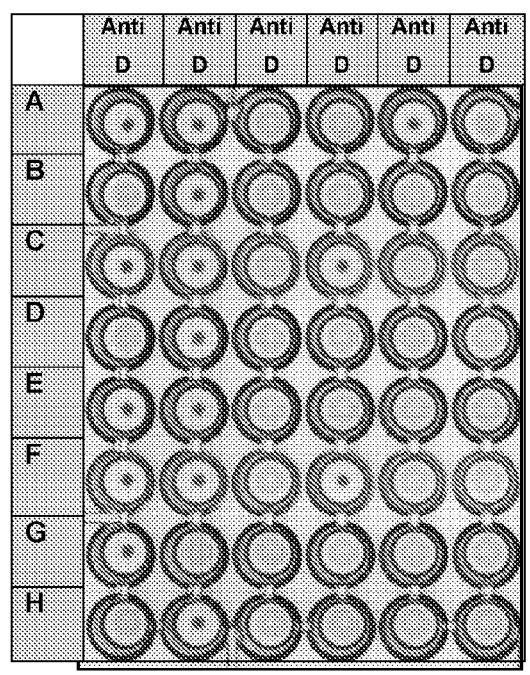

FIG. 16: Immunoadherence method for the Weak D phenotyping of 48 donors

FIG. 17: Improvement of the sensitivity and the specificity of the cross-match test, by reducing the anti-GPA concentration coupled to magnetic beads. Comparative study.

FIG. 18: Stability study between 2 concentrations of non ionic detergent (0.5% vs 5%) during the storage of magnetic particles coupled to anti-GPA.

EXAMPLE 1

Material and Methods

Figure 8:
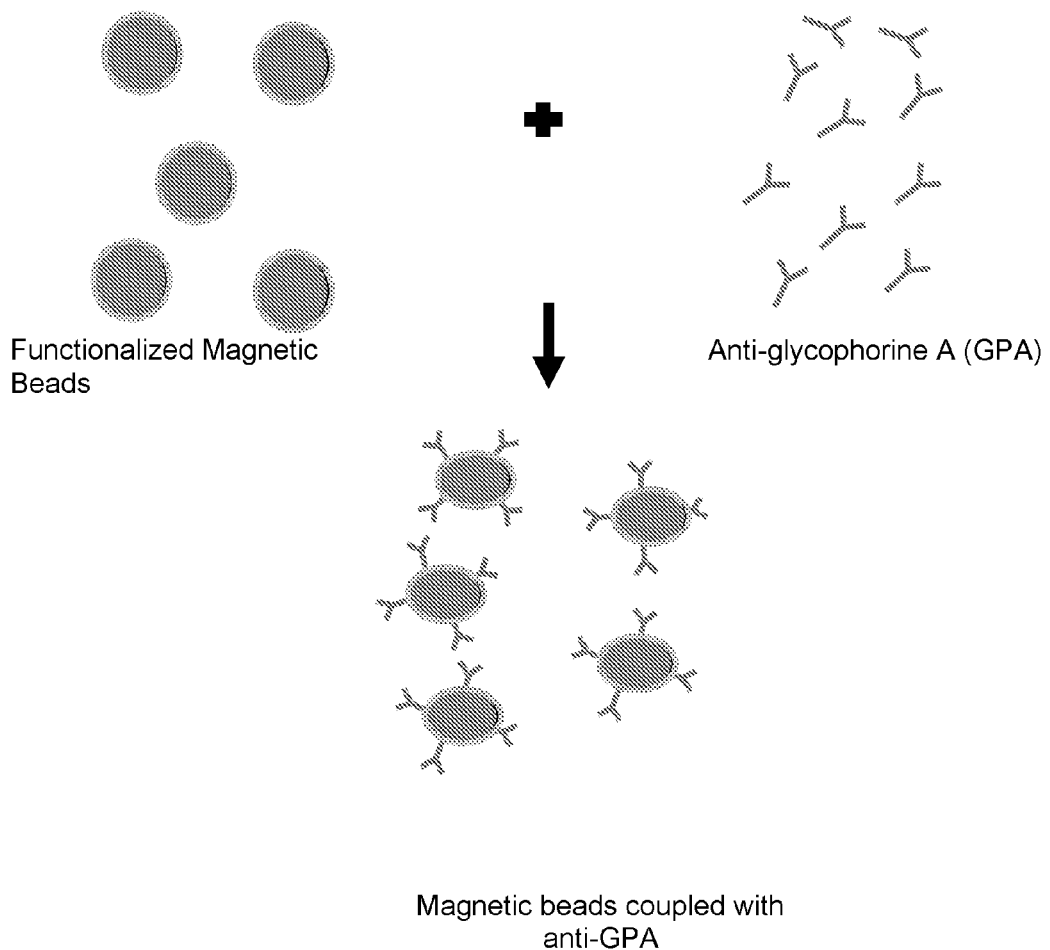

A) Example of Coupling of the Anti-Glycophorin A to Magnetic Beads Tosylactivated (See FIG. 8)

The coupling of the anti-glycophorin A to magnetic particles tosylactivated from ESTAPOR™ (reference: R01-24) can be performed either with a 0.1M sodium borate buffer pH9.5, or with 0.1M phosphate buffer pH 7.4.

Before the coupling, magnetic particles Tosylactivated are washed twice using a magnet in the coupling buffer chosen. The coupling is performed by resuspending the beads in the coupling buffer (borate or phosphate) and by adding the antibody at a concentration of 10 µg per mg of beads. The coupling of the antibody is performed in presence of 3M ammonium sulfate.

25 mg of Tosyl magnetic particles (ie 250 µl of beads at 10% w/v) are washed twice using a magnet in 0.1M phosphate buffer pH 7.4 or 0.1M sodium borate buffer pH 9.5.

Pipette off carefully the supernatant, once the beads have migrated to the magnet and the liquid is clear Remove the tube from the magnet and resuspend the beads with 10 µg of anti-glycophorin A Add 250 µl 3M ammonium sulfate to the suspension of beads to achieve a final concentration of 1.5 M ammonium sulfate Resuspend the beads thoroughly by vortexing Incubate for 24 h-48 h at room temperature with slow tilt rotation.

At the end of the coupling, place the tube on a magnet and pipette off the supernatant carefully once the beads have migrated to the magnet and the liquid is clear.

Remove the tube from the magnet and resuspend the beads in a blocking buffer containing 0.3M phosphate buffer saline (PBS) with 0.5% BSA (w/v).

Incubate for 2 hours at room temperature with slow tilt rotation.

At the end of the blocking step, place the tube on a magnet and pipette off the supernatant carefully once the beads have migrated to the magnet and the liquid is clear.

Remove the tube from the magnet and resuspend the beads with a preservative solution containing 0,3M PBS with 0.1% (w/v) BSA and 0.5% (w/v) of Synperonic™ PE/F68.

The final concentration of the beads coupled with anti-glycophorin A is 1% (w/v) in the preservative buffer. Beads are store at 4° C. until use.

B) Example of Coupling of the Anti-Glycophorin A to Magnetic Beads Carboxylic Acid from ESTAPOR™

The preferred method of coupling of the anti-GPA to the magnetic beads carboxylic acid from ESTAPOR™ is by physical adsorption (ref: M1-030/40.)

The concentration of anti-GPA used varies from 5 µg to 25 µg per mg of beads with a preference for 10 µg of anti-GPA per mg of beads.

The coupling of anti-GPA to the magnetic beads carboxylic acid is carried out as follow:

25 mg of magnetic particles carboxylic acid (ie 250 µl of beads at 10% w/v) are washed twice using a magnet in 1 ml of 10 mM phosphate buffer pH6.

At the end of the washing step, place the tube on a magnet and pipette off the supernatant carefully once the beads have migrated to the magnet and the liquid is clear Remove the tube from the magnet and resuspend the beads using 1.5 ml of 20 mM phosphate buffer pH 7.5.

Add immediately the anti-GPA at a concentration of 10 µg per mg of beads.

Mix thoroughly by vortexing

Incubate for 2 hours at room temperature with a slow tilt agitation

Place the tube on a magnet and pipette off the supernatant carefully once the beads have migrated to the magnet and the liquid is clear.

Wash 3 times the beads with 20 mM phosphate buffer pH7.5 placing the tube on the magnet.

At the end of the washing step, resuspend the beads in a blocking buffer containing 0.3 M phosphate buffer saline (PBS) with 0.5% BSA (w/v).

Incubate for 2 hours at room temperature with a slow tilt agitation

At the end of the blocking step, place the tube on a magnet and pipette off the supernatant carefully once the beads have migrated to the magnet and the liquid is clear.

Remove the tube from the magnet and resuspend the beads with a preservative solution containing 0,3M PBS with 0.1% (w/v) BSA and 0.5% (w/v) of Synperonic™ PE/F68.

The final concentration of the beads coupled with anti-glycophorin A is 1% (w/v) in the preservative buffer. Beads are store at 4° C. until use.

C) Example of Coupling of the Anti-Glycophorin A to Magnetic Beads Carboxylic Acid from JSR Micro The preferred method of coupling of the anti-GPA to the magnetic beads carboxylic acid from JSR Micro is by physical adsorption (ref.: Magnospheres MB100).

The concentration of anti-GPA used varies from 5 µg to 25 µg per mg of beads with a preference for 20 µg of anti-GPA per mg of beads.

The coupling of anti-GPA to 5 mg of magnetic beads carboxylic acid is carried out as follow:

5 mg of magnetic particles carboxylic acid (ie 50 µl of beads at 10% w/v) are washed twice using a magnet in 200 µl of 50 mM MES buffer (2-(N-morpholino) Ethane Sulfonic Acid), pH6.2

At the end of the washing step, place the tube on a magnet and pipette off the supernatant carefully once the beads have migrated to the magnet and the liquid is clear Add immediately the anti-GPA at a concentration of 20 µg per mg of beads.

Mix thoroughly by vortexing

Incubate for 2 hours at room temperature with a slow tilt agitation

Place the tube on a magnet and pipette off the supernatant carefully once the beads have migrated to the magnet and the liquid is clear.

Wash 3 times the beads with 50 mM MES buffer pH 6.2 placing the tube on the magnet.

At the end of the washing step, resuspend the beads in a blocking buffer containing 0.3M phosphate buffer saline (PBS) with 0.5% BSA (w/v).

Incubate for 2 hours at room temperature with a slow tilt agitation

At the end of the blocking step, place the tube on a magnet and pipette off the supernatant carefully once the beads have migrated to the magnet and the liquid is clear.

Remove the tube from the magnet and resuspend the beads with a preservative solution containing 0,3M PBS with 0.1% (w/v) BSA and 0.5% (w/v) of Synperonic™ PE/F68.

The final concentration of the beads coupled with anti-glycophorin A is 1% (w/v) in the preservative buffer. Beads are store at 4° C. until use.

D) Dilution of the Beads Coupled in the Diluents

Once the beads coupled to anti-GPA, these one are directly diluted in the diluent Liss and Ficoll™ 2% (w/v), which is then distribute on the top of the viscous solution or gel. The concentration of the beads in the diluent can vary between 0,005% and 0.02%, with a preference for 0.004%.

EXAMPLE 2

Coating of the Inclined Wall and Cupule Base with an Anti-Human Immunoglobulin (AHG)

The chemical and physico-chemical nature of the plastic used for the cupules makes it possible to cover the latter with a layer of human anti-immunoglobulin (monoclonal or polyclonal HAG type) capable of specific binding to the antibodies of any specific complexes that may be formed when the antibody of said complex is of human origin.

Moreover, it can be noted that this HAG composition can include antibodies directed against complement-type serum protein determinants.

The surfaces of the internal wall of the container which are not coated with AHG can be saturated using conventional saturating agents in solid phase or ELISA (Enzyme Linked Immunosorbent Assay) type techniques.

For example, the AHG solution at a concentration between 1 and 10 µg/ml can be prepared in a 0.2 M carbonate buffer pH 9.6.

This solution is distributed at a volume of 75 µl in each cupule of a round-based Maxisorp NUNC U8 type microplate. The plates are then incubated overnight at 4° C.

The cupules are then washed using a phosphate buffer solution (PBS 2.5 mM, pH 7.4) in order to eliminate any proteins not directly adsorbed onto the plastic.

The cupules are then treated with an albumen solution at 30 g/l in PBS buffer at a rate of 100 µl per cupule.

After incubation for 2 hours at room temperature, the cupules are washed again in phosphate buffer.

EXAMPLE 3

1st Method: Magnetisation of the Red Blood Cells with the Magnetic Beads Coupled to Anti-GPA (Anti-Glycophorin A) in a Separate Well (See FIG. 9 for the General Principle of Magnetization and FIG. 10 for Method 1)

Detection of irregular antibodies consists of using red blood cells with known phenotypes called panel. A panel consists of three complementary phenotypes of cells. In three wells of a 96-well microtiter round bottom is deposited 5 µl of beads coupled to anti-GPA, then add 45 µl of each red cell panel diluted to 1% in a storage buffer.

After mixing the two components, red cells are immediately magnetized and ready to be used in following steps.

In three wells of a microplate of 96 wells round bottom, coated with a specific anti-human globulin (anti-IgG) or a mixture of anti-human globulin (anti-IgG and anti-IgM), a viscous solution or a gel with a density greater than 1, is deposit and can make a barrier between the reaction medium containing the cells and the serum test and the antiglobulin.

On the top of the barrier is deposited a viscous diluent with a density greater than 1, on which will be deposited magnetized cells via anti-GPA, as well as serum or plasma from the patient or donor to be tested.

The microplate is then incubated at 37° C. for 20 minutes. During this incubation the red cell antibodies present or not in serum, will bind to the magnetized red cell carrying the antigens. At the end of incubation, the microplate is placed on a rotary stirrer equipped with a magnetic plate. During application of the magnetic field simultaneously with stirring, magnetized erythrocytes which are carrying or not anti-erythrocyte antibody on their surface, will drawn through the viscous solution and will be bind or not on the AHG coated on the bottom.

The final stirring under magnetic field consists in 2 sequences: the first stirring sequence allows to the magnetized and sensitized red blood cells to be captured by the anti-globulins and last between 2 min 30 sec and 4 minutes at 500 rpm with a preference for 3 minutes at 500 rpm, while the second stirring sequence allows to form the negative reaction by the formation of a pellet, this sequence last between 30 sec and 2 minutes at 600 rpm with a preference for 1 min at 600 rpm.

In the case of a positive reaction, the magnetized cells sensitized with patient or donor serum (or plasma), will bind to AHG and form a thin layer of erythrocytes at the bottom of the well.

In the case of a negative reaction, the magnetized cells sensitized with patient or donor serum (or plasma), will then form a pellet at the bottom of the well (see FIG. 3).

EXAMPLE 4

2nd Method: Magnetization of Red Blood Cells with Magnetic Beads Coupled to Anti-GPA During the Sensitization by Serum or Plasma. Successive Deposit of Each Element (See FIG. 11)

In three wells of a microplate of 96 wells round bottom, coated with a specific anti-human globulin (anti-IgG) or a mixture of anti-human globulin (anti-IgG and anti-IgM), a viscous solution or a gel with a density greater than 1, is deposit and can make a barrier between the reaction medium containing the cells and the serum test and the antiglobulin.

Deposit of a diluent on the top of the viscous barrier or gel, then deposit of the magnetic beads coupled to anti-GPA, then red blood cells diluted to 1% in their storage buffer and finally deposit of the patient (or donor) plasma or serum to be tested.

The microplate is then incubated at 37° C. during 20 minutes. During the incubation, magnetic beads coupled to anti-GPA will bind to the red blood cells; this is the same for the irregular antibodies present or not in the serum or plasma to be tested. Each antibody being specific of an antigen, the binding of one to red cells does not bother the binding of the other one.

Thus, the red blood cells bearing antigens could be both magnetized and sensitized by the antibodies present or not in patient's plasma.

At the end of the incubation, the microplate is placed on a rotary stirrer equiped with a magnetic plate. With the application of the magnetic field simultaneously with the stirring, red blood cells carrying or not irregular antibodies, will drawn through the viscous solution and will be bind or not on the AHG coated on the bottom. The final stirring under magnetic field consists in 2 sequences: the first stirring sequence allows to the magnetized and sensitized red blood cells to be captured by the anti-globulins and last between 2 min 30 sec and 4 minutes at 500 rpm with a preference for 3 minutes at 500 rpm, while the second stirring sequence allows to form the negative reaction by the formation of a pellet, this sequence last between 30 sec and 2 minutes at 600 rpm with a preference for 1 min at 600 rpm.

As in the previous example, in the case of a positive reaction, the magnetized cells sensitized with patient or donor serum (or plasma), will bind to AHG and form a thin layer of erythrocytes at the bottom of the well. In the case of a negative reaction, the magnetized cells sensitized with patient or donor serum (or plasma), will then form a pellet at the bottom of the well.

In this method, there is no need to carry out the magnetization of red blood cells in a separate well, since the magnetization is specific (via anti-GPA antibody) no interference can occur during this latter, so the sensitization of the red blood cells by patient's plasma can occur independently.

EXAMPLE 5

3rd Method: Magnetization of Red Blood Cells with Magnetic Beads Coupled to Anti-GPA During the Sensitization by Serum or Plasma. Dilution of the Magnetic Beads Coupled to GPA in the Diluent. (See FIG. 12)

In this method, which is preferred to the two others, the beads are directly diluted in the diluent to be deposited on the filter. Thus the number of deposit is limited and the diluent containing the beads coupled with anti-glycophorin A is regarded as a reagent.

As before, in 3 wells of a microplate of 96 wells round bottom, coated with a specific antihuman globulin (IgG) or a mixture of anti-human globulin (anti-IgG and anti-IgM), a viscous solution or gel with a density greater than 1, was introduced and can be a barrier between the reaction medium containing the cells and the serum test and the antiglobulin. The diluent containing the magnetic beads coupled with anti-GPA is deposed on the top of the viscous barrier or gel. Then red blood cells diluted to 1% in their storage buffer are deposed on the diluent containing the magnetic beads and finally the plasma or serum of the patient (or donor) to be tested is deposed above the red blood cells.

In a preferred embodiment, red blood cells have been already mixed to the diluent containing the magnetic beads coupled to the anti-GPA, before being deposited on the top of the viscous barrier of a density greater than 1. Then the plasma or serum is added to the mix red blood cells—diluent—magnetic beads.

In an automated embodiment, is preferred as follows: in 3 wells of a microplate of 96 wells, round bottom, coated with a specific antihuman globulin (IgG) or a mixture of anti-human globulin (anti-IgG and anti-IgM) the red blood cells are deposited, and the diluent containing the magnetic beads. The two components are mixed by placing the plate on an automatic stirrer. At the end of the stirring, the viscous barrier of high density is injected under the mix red blood cells—diluent—magnetic beads by placing the tips of the automate at the bottom of the wells. Due to its density, the viscous barrier remains under the mix, thus avoiding the saturation of the AHG by non-specific antibodies, whereas the mixture formed by the cells and the diluent containing the magnetic beads, less dense remains above the viscous barrier.

This gives two distinct phases with different densities: the first being the higher density gel over the AGH and diluent containing magnetic beads coupled to anti-GPA and mixed with red blood cells. Then the patient's plasma to be tested will be placed over the mixture.

The microplate is then incubated at 37° C. for 20 minutes. During incubation, the irregular antibodies present or not in the tested plasma will bind to red cells. The red blood cells bearing antigens could be both magnetized and sensitized by the antibodies present or not in patient's plasma. Each antibody being specific of an antigen, the binding of one to red cells does not bother the binding of the other one.

At the end of the incubation, the microplate is placed on a rotary stirrer equipped with a magnetic plate. With the application of the magnetic field simultaneously with the stirring, red blood cells carrying or not irregular antibodies, will drawn through the viscous solution and will be bind or not on the AHG coated on the bottom. The final stirring under magnetic field consists in 2 sequences: the first stirring sequence allows to the magnetized and sensitized red blood cells to be captured by the anti-globulins and last between 2 min 30 sec and 4 minutes at 500 rpm with a preference for 3 minutes at 500 rpm, while the second stirring sequence allows to form the negative reaction by the formation of a pellet, this sequence last between 30 sec and 2 minutes at 600 rpm with a preference for 1 min at 600 rpm.

As in the previous example, in the case of a positive reaction, the magnetized cells sensitized with patient or donor serum (or plasma), will bind to AHG and form a thin layer of erythrocytes at the bottom of the well. In the case of a negative reaction, the magnetized cells sensitized with patient or donor serum (or plasma), will then form a pellet at the bottom of the well.

All these methods of magnetization can be declined on other tests, such as testing for compatibility between donor and recipient.

In this case, the donor cells from the transfusion bag, are previously diluted to 1% in a buffer of low ionic strength, before being placed on the diluent containing magnetic beads coupled to anti-GPA.

It is the same for the direct coombs test, performed in patients suspected to have been sensitized in vivo by irregular antibodies, especially in cases of foeto-maternal incompatibilities or auto-immune hemolytic diseases.

In these cases, red cell sensitized in vivo are previously diluted to 1% in a buffer of low ionic strength, before being placed on the diluent containing magnetic beads coupled to anti-GPA.

EXAMPLE 6

Detection Test of Irregular Antibodies Using the Method No 3 (See FIG. 4)

The beads coupled with anti-GPA, are diluted directly into the diluent (also called Liss Ficoll), itself deposited on the viscous barrier or gel (also called Nanolys™) of superfine Sephadex™ G-100 type at 3% in a solution of 10% albumin in Liss. The cells are either from a primary tube of the patient group O and diluted to 1% in a buffer of low ionic strength, or from a panel of red cells of group O, diluted to 1% in a storage buffer.

The antiserum used (test serum), comes from a patient and contains irregular antibodies such as anti-D+anti-C+anti-E. This sample is tested at different dilutions.

The expected results were carried out on a technique already commercialized using the same cells and the same anti-serum.

Protocol:

In the wells of a 96-well microtiter round bottom coated with a human anti-globulin (anti-IgG) (also called Screen-Lys™) 50 µl of Nanolys™ is deposited, add then 50 µl of Liss Ficoll containing magnetic beads coupled to anti-GPA. Add 15 µl of red blood cells diluted to 1% and finally add 15 µl of serum or plasma to be tested. Place the microplate in the incubator at 37° C. for 20 minutes, and then place the microplate on a stirrer equipped with a plate of magnets fitting exactly under each well of the microplate. The final stirring under magnetic field consists in 2 sequences: 3 minutes at 500 rpm follows by 1 min at 600 rpm.

EXAMPLE 7

Titration of an Anti-D from CNRGS (French National Reference Centre for Blood Groups) Using Detection Test of Irregular Antibodies (See FIG. 5)

Use of dilution series of anti-D standard from CNRGS, as antiserum tested with group O red blood cell panels diluted to 1% in buffer conservative.

This titration of standard anti-D allows demonstrating the detection threshold of the described method.

Protocol:

In the wells of a Screenlys™ (plate coated with a human anti-globulin (anti-IgG)) 50 µl of Nanolys™ is deposited, and then 50 µl of Liss Fioll containing magnetic beads coupled to anti-GPA is added on the Nanolys™. Add 15 µl of red blood cells diluted to 1% and finally add 15 µl of each dilution of anti-D to be tested. The plate is then incubated at 37° C. for 20 minutes, and then placed on a stirrer equipped with a plate of magnets fitting exactly under each well of the microplate. The final stirring under magnetic field consists in 2 sequences: 3 minutes at 500 rpm follows by 1 min at 600 rpm.

The results show that the test of detection of irregular antibodies is sensitive and capable of detecting up to 1.25 ng/ml of anti-D.

This method of magnetization is quite comparable in sensitivity and specificity to methods already commercialized.

EXAMPLE 8

Cross Match Test (Compatibility Test) Performed on Group O Red Blood Cell Donors (See FIGS. 6 and 7)

Group O red blood cell from donors collected on EDTA tubes, are tested against the plasma or serum from patients likely to contain or not irregular anti-erythrocyte antibodies.

The results are presented below.

Protocol:

From primary tube donor, 10 µl of packed red blood cells are diluted in 1 ml of low ionic strength buffer, to make a 1% erythrocyte suspension.

In the wells of a ScreenLys™ (plate coated with a human anti-globulin (anti-IgG)) 50 µl of Nanolys™ is deposited, and then 50 µl of Liss Ficoll containing magnetic beads coupled to anti-GPA is added on the Nanolys™. Add 15 µl of red blood cells diluted to 1% and finally add 15 µl of the patient's plasma or serum to be transfused. The plate is then incubated at 37° C. for 20 minutes, and then placed on a stirrer equipped with a plate of magnets fitting exactly under each well of the microplate. The final stirring under magnetic field consists in 2 sequences: 3 minutes at 500 rpm follows by 1 min at 600 rpm.

The results obtained in this method of magnetization using magnetic beads coupled to an antibody specific for red blood cells can clearly demonstrate the capability to determine blood compatibility between donor and recipient, in different blood systems.

EXAMPLE 9

Blood Grouping/Phenotyping Including the Simonin Test, Method Using Agglutinating Antibodies of IgM Type A) Agglutination Method Prior to carrying out the test, a magnetizing solution is realized by diluting magnetic beads coupled with anti-GPA in a Phosphate buffer 0.3M containing 0.1% of BSA (w/v) and 0.5% of Synperonic™ PE/F68. The concentration of magnetic beads coupled with anti-GPA can vary from 0.001% to 0.004%, preferably at 0.003%.

In the case of a direct test or Beth-Vincent test, monoclonal antibodies specific to red blood cell antigens from ABO system (anti-A, anti-B and anti-AB), from Rhesus system (D, C, c, E, e) and from Kell antigen are dried in the round-shaped bottom wells of a 96 wells microplate.

The implementation of the typing for antigens of interest on the red cells of an individual is carried out on a blood sample collected in tube with anticoagulant such as EDTA, Citrate or Heparin.

A globular suspension between 0.5% and 1.2%, preferably at 1% is carried out, in a tube or in the well of a round-shaped bottom microplate, by diluting 10 µl of globular pellet in 1 ml of a low ionic strength buffer, in particular a LISS buffer.

In the wells of a microplate of 96 round-shaped bottom wells containing the dessicated antiserums mentioned above, 10 µl of magnetizing solution are deposited, to which 30 µl of globular suspension at 1% are added.

At the same time as the direct test, the Simonin test is carried out in the unused adjacent wells: 10 µl of a magnetizing solution containing magnetic beads coupled with anti-GPA, are thus, deposited in the 4 unused wells, then 15 µl of a suspension of test red blood cells, of known blood group such as from A1, A2, B, or O group, previously diluted at 1% in a storage buffer of low ionic strength, are added to the beads and finally 25 µl of plasma of patient or donor to be phenotyped are added.

The components are homogenized by placing the microplate on a automatic microplate stirrer. The agitation speed can vary between 500 and 800 rpm, preferably between 650 and 750 rpm, preferably at 700 rpm. The duration of agitation can vary between 1 min and 2 min with a preference for 1 min 30 sec.

The microplate is then incubated between 2 min and 15 minutes with a preference for 10 minutes at room temperature.

Each antibody being specific to an antigen, the binding of one does not prevent the binding of the other one. Thus the red blood cells bearing the erythrocyte antigens could be both magnetized by the anti-GPA beads and sensitized by the antisera dessicated in the wells.

At the end of the incubation step, the microplate is put on a plate with 96 magnets fitting perfectly in each well of the microplate. Under the influence of the magnetic field, the red blood cells sensitized and magnetized through the anti-GPA, will be drawn at the bottom of the wells and will form a pellet if the antigen corresponding to the antiserum is present. The duration of the magnetization can vary between 3 min and 7 min, with a preference for 5 minutes at room temperature.

The microplate is then placed on a stirrer to suspend non-agglutinated red blood cells i.e RBC that are negative for the screened antigen. The sequence of agitations allows both the re-suspension of non-agglutinated red blood cells and the visualization of red blood cells agglutinates as follows: the first, fairly strong stirring pulls the packed red blood cells off the bottom of the wells after magnetization. This stirring is carried out for 1 to 2 min 30 sec at a speed ranged between 800 and 1000 rpm, preferably 1 min 45 sec at 900 rpm. At the end of stirring, the non-agglutinated red blood cells are dispersed forming a homogeneous suspension, while the red blood cells expressing the screened antigen form a compact agglutinate.

Nevertheless for the more slightly expressed antigens the formed agglutinates are smaller and more dispersed at the end of stirring, requiring a so-called <<recollection>> stirring that will assemble all the small dispersed agglutinates to form thus a complete, clearly-defined agglutinate at the bottom of the well. This so-called <<recollection>> stirring is performed at low speed i.e at between 350 to 550 rpm during 30 sec to 1 min, preferably 450 rpm during 45 sec. This <<recollection>> stirring has no effect on the negative red blood cells or on the strong agglutinates. The microplate can then be read off by the naked eye or by an automatic reader equipped with a camera.

A positive reaction will lead to the presence of one or several agglutinates at the bottom of the wells, whereas a negative reaction will lead to a homogeneous suspension of red cells.

EXAMPLE 10

Microplate of DUOLYS Type, Enabling to Carry Out, ABO Grouping and Rh-K Phenotyping Tests, on 8 Patients, Test Including the Simonin Test with A1 and B Tests Red Blood Cells A) Reagents:
  DuoLys microplate containing the dried out antibodies of group
  a bottle of magnetizing solution containing magnetic beads coupled with anti-GPA and diluted at 0.004% in a phosphate buffer 0.3 M+0.1% BSA (w/v)+0.5% Synperonic™ (w/v) PE/F68
  a suspension of tests red blood cells of A1 group diluted at 1% in a storage buffer
  a suspension of tests red blood cells of B group diluted at 1% in a storage buffer
  8 blood samples from patients collected on anticoagulant of EDTA
B) Protocol: For Each Blood Sample
  Deposit of 10 µl of magnetizing solution in each well 1 to 12.
  In wells 1 to 10: deposit of 30 µl of globular suspension at 1% carried out in Liss.
  In the column 11: deposit of 5 µl of test red blood cells suspension from A1 group
  In the column 12: deposit of 5 µl of test red blood cells suspension from B group
  In wells 11 and 12: deposit of 25 µl of plasma from each patient
  Agitation of the microplate for 1 min 30 sec at 700 rpm
  Incubation of the microplate at room temperature for 10 minutes
  Magnetization of the microplate on a magnet plate for 5 minutes
  Agitations: 1 min 45 sec at 900 rpm+45 sec at 450 rpm
  Reading with naked eye and by means of a camera
C) Results (See FIG. 13)
  The results obtained in this method of magnetization using magnetic beads coupled to an antibody specific for red blood cells can clearly demonstrate the capability to determine the blood grouping and the Rh-K phenotype, including the reverse test (Simonin test), in case of dried anti-sera.

EXAMPLE 11

Blood Phenotyping, Method Using Antibodies of IgG and/or IgM Type, Technique by Agglutination The present invention also enables to carry out an red blood cells grouping/phenotyping from IgG and/or IgM test in liquid form. When the anti-serum is of IgG type, an <<agglutinative>> reagent is prepared from an anti-IgG anti-immunoglobulin previously saturated with a specific anti-IgG concentrated solution of the searched antigen.

This liquid <<agglutinative>> reagent is thus used during the blood phenotyping such as any other phenotyping reagent.

Prior the realization of the test, a reagent of agglutinative type is prepared from incubating an anti-IgG anti-immunoglobulin with a nonpurified monoclonal antibody concentrate containing IgG anti-red blood cells (RBC) antibodies.

A globular suspension between 0.5% and 1.2%, by preference 1% is prepared in a tube or in the well of a microplate with a round bottom, by diluting 10 µl of packed RBC in 1 ml of low ionic strength buffer, in particular a LISS buffer.

In a microplate of 96 wells with round bottom, 10 µl of magnetizing solution are deposited, to which 15 µl of globular suspension at 1% are added and 25 µl of anti-RBC <<agglutinative>> reagent of IgG or IgM type.

The components are homogenized by placing the microplate on a microplate stirrer. The speed of agitation can vary from 1000 to 1200 rpm, with a preference for 1200 rpm. The duration of agitation can vary from 5 sec to 1 min with a preference for 10 sec.

The microplate is then incubated from 10 min to 30 minutes with a preference for 20 minutes at 37° C.

Each antibody being specific to an antigen, the binding of the first does not prevent the binding of the other. Thus the red blood cells bearing the erythrocytic antigens could be magnetized by the anti-GPA beads as well as sensitized by anti-serums of IgM of IgG type deposited at the bottom of the wells.

At the end of the incubation step, the microplate is placed on a plate containing 96 battery magnets that adjust perfectly beneath each well of the microplate. Under the influence of the magnetic field, the red blood cells that are sensitized and magnetized by means of anti-GPA, will be drawn at the bottom of the wells and will form an agglutinate if the antigen corresponding to the anti-serum is present. The duration of the magnetization can vary from 5 min to 15 min with a preference for 10 minutes at room temperature.

Then the microplate is placed on a microplate stirrer to enable the resuspension of the non agglutinated red cells, so negative for the searched antigen. The sequence of agitations allows both the resuspension of non-agglutinated red blood cells and the visualization of RBC agglutinates as follows: the first, fairly strong stirring pulls the packed red blood cells off the bottom of the wells after magnetization. This stirring is performed for 1 to 2 min 30 sec at a speed between 500 and 1000 rpm, with a preference for 1 min 30 sec at 700 rpm. At the end of the agitation step, the non-agglutinated red blood cells are dispersed and form an homogeneous suspension, whereas the red blood cells corresponding to the searched antigen form a compact agglutinate. For less strongly expressed antigens, the agglutinates formed are smaller and more dispersed at the end of stirring, requiring a so-called "re-collection" stirring that will assemble all the small, dispersed agglutinates to form a complete, clearly-defined agglutinate at the bottom of the well. This so-called recollection stirring is performed at low speed, i.e at a speed between 350 and 550 rpm for 30 sec to 1 min, with a preference for a speed of 450 rpm for 45 sec. The so-called re-collection stirring has no effect on the negative RBCs or the strong agglutinates. The microplate can then be read off by the naked eye or by an automatic reader equipped with a camera.

A) Reagents
  A bottle of magnetizing solution containing magnetic beads coupled with anti-GPA and diluted at 0.005% in a PBS 0.3 M+0.1% BSA (w/v)+0.5% (w/v) synperonic PE/F68

A bottle of polyclonal solution of anti-Jkb antibody (clone P.143, IgM type)

A bottle of anti-S <<agglutinative>> reagent: 1 ml of AGH (concentration=1.8 mg/ml)+20 ml of concentrated solution of anti-S (clone P3S13JS123, IgG type)

A bottle of anti-s <<agglutinative>> reagent: 1 ml of AGH (concentration=1.8 mg/ml)+20 ml of concentrated solution of anti-s antibody (clone P3YAN3, IgG type)

5 blood samples from patients collected on anticoagulant of EDTA

B) Protocol: For Each Blood Sample

Deposit of 10 µl of magnetizing solution in 3 wells of a microplate of 96 round-bottom wells.

Addition in the 3 said wells of 15 µl of globular suspension at 1% carried out in Liss.

Addition of 25 µl of anti-Jkb reagent, anti-S and anti-s in each of the 3 wells.

Stirring of the microplate for 10 sec at 1200 rpm

Incubation of the microplate at 37° C. for 20 minutes

Magnetization of the microplate on a magnet plate for 10 minutes

Stirrings: 1 min 30 sec at 700 rpm+45 sec at 450 rpm

Reading with a naked eye and with a camera.

C) Results: See FIG. 14

The results obtained in this method of magnetization using magnetic beads coupled to an antibody specific for red blood cells can clearly demonstrate the capability to determine the extended phenotype of donors or patients, in different blood systems.

EXAMPLE 12

Extended Phenotyping of 8 Donors: Use of Anti-Fya, Anti-Fyb, Anti-Jka, Anti-Jkb, Anti-S and Anti-s Anti-Serums Using of Immuno-Adherence Technique Method A) Reagents:

Diluent made of a sugar-based polymer and a low ionic strength buffer, in which are diluted with the beads coupled with anti-GPA. The concentration of this diluent containing the beads is at 0,004% anti-Fya human monoclonal antibody (clone DGFYA02, of IgG type)

anti-Fyb human polyclonal antibody anti-Jka human monoclonal antibody (clone P3HT7, of IgM type)

anti-Jkb human monoclonal antibody (clone P.143, of IgM type)

anti-S human monoclonal antibody (clone, P3S13JS123, of IgG type)

anti-s human monoclonal antibody (clone, P3YAN3, of IgG type)

Negative Control

Nanolys 8 donors blood samples collected on anticoagulant of EDTA type

B) Protocol: For Each Donor

Prior the tests, the beads coupled with anti-GPA are diluted directly into the diluent (also called Liss Ficoll).

The red blood cells from 8 donors are diluted at 1% in the diluent containing the beads coupled with anti-GPA. The different suspensions are carried out in a tube or in the well of a 96 round bottom deepwells of a microplate.

In 7 wells of a 96-well microtiter round bottom coated with a mix of IgG and IgM human anti-globulins (anti-IgG) (also called CrossLys™) 50 µl of a viscous barrier or gel (also called Nanolys™) is deposited. Above the Nanolys™, 55 µl of the globular suspension at 1% in the diluent containing the beads, is deposited. Finally, 10 µl of each anti-serum are deposited above the globular suspension. Then the microplate is incubated for 20 minutes at 37° C. At the end of the incubation the microplate is place on a stirrer equipped with a plate of magnets fitting exactly under each well of the microplate. With the application of the magnetic field simultaneously with the stirring, red blood cells carrying or not irregular antibodies, will drawn through the viscous solution and will be bind or not on the AHG coated on the bottom. The final stirring under magnetic field consists in 2 sequences: the first stirring sequence allows to the magnetized and sensitized red blood cells to be captured by the anti-globulins and last 3 minutes at 500 rpm, while the second stirring sequence allows to form the negative reaction by the formation of a pellet, this sequence last 1 min at 600 rpm.

In the case of a positive reaction, the magnetized cells sensitized with anti-sera, will bind to AHG and form a thin layer of erythrocytes at the bottom of the well. In the case of a negative reaction, the magnetized cells sensitized with anti-sera, will then form a pellet at the bottom of the well.

The expected results were carried out on a technique already commercialized using the same cells and the same antiserum.

C) Expected Results: See Table Below

|  | Fya | Fyb | Jka | Jkb | S | s | CTL |
|---|---|---|---|---|---|---|---|
| Patient #1 | 1 | 1 | 0 | 1 | 0 | 1 | 0 |
| Patient #2 | 1 | 0 | 1 | 1 | 0 | 1 | 0 |
| Patient #3 | 1 | 1 | 1 | 0 | 0 | 1 | 0 |
| Patient #4 | 0 | 0 | 1 | 0 | 1 | 1 | 0 |
| Patient #5 | 1 | 0 | 0 | 1 | 0 | 1 | 0 |
| Patient #6 | 0 | 1 | 0 | 1 | 1 | 1 | 0 |
| Patient #7 | 1 | 1 | 1 | 1 | 0 | 1 | 0 |
| Patient #8 | 0 | 1 | 1 | 1 | 0 | 1 | 0 |

Obtained Results: See FIG. 15

The results obtained in this method of magnetization using magnetic beads coupled to an antibody specific for red blood cells can clearly demonstrate the capability to determine the extended phenotype of donors or patients, in different blood systems.

EXAMPLE 13

Phenotyping of 48 Donors for the Weak D Antigen. Use of a Mix of 2 Different Clones Anti-D (FIG. 4) Using of Immuno-Adherence Technique Method A) Reagents Diluent made of a sugar-based polymer and a low ionic strength buffer, in which are diluted with the beads coupled with anti-GPA. The concentration of this diluent containing the beads is at 0.004%

Mix of anti-D (clone ESD1 and clone P3x35)

Nanolys 48 donors blood samples collected on anticoagulant of EDTA type

B) Protocol: For Each Donor

The protocole for the extended phenotyping can be carried out, for the weak D test.

C) Expected Results: See Table Below

|   | Anti D | Anti D | Anti D | Anti D | Anti D | Anti D |
|---|--------|--------|--------|--------|--------|--------|
| A | D−     | D−     | D+     | D+     | D−     | Dw Typ |
| B | Dw Type1 | D−   | D+     | D+     | D+     | DMH    |
| C | D−     | D−     | D+     | D−     | D+     | D+     |
| D | Dw Type3 | D+   | D+     | D+     | D+     | D+     |
| E | D−     | D−     | DAU    | D+     | D+     | D+     |
| F | D−     | D−     | D+     | D−     | D+     | Dw Type3 |
| G | D−     | D+     | D+     | Dw Type3 | D+   | D+     |
| H | Dw Type3 | D−   | DVII   | D+     | D+     | D+     |

D) Obtained Results:

The results obtained in this method of magnetization using magnetic beads coupled to an antibody specific for red blood cells can clearly demonstrate the capability to determine the weak D phenotype of donors.

EXAMPLE 14

Improvement of the Sensitivity and Specificity of the Tests by Reducing the Anti-GPA Concentration Coupled to the Magnetic Particles A) Coupling of the Anti-Glycophorin A to Magnetic Beads Carboxylic Acid from JSR Micro The preferred method of coupling of the anti-GPA to the magnetic beads carboxylic acid from JSR Micro is by physical adsorption (ref: Magnospheres MB100).

To increase the specificity and sensitivity of the tests, the concentration of anti-GPA used varies from 2 µg to 5 µg per mg of beads with a preference for 2.5 µg of anti-GPA per mg of beads.

The coupling of anti-GPA to 5 mg of magnetic beads carboxylic acid is carried out as follow:
  5 mg of magnetic particles carboxylic acid (ie 50 µl of beads at 10% w/v) are washed twice using a magnet in 200 µl of 50 mM MES buffer (2-(N-morpholino) Ethane Sulfonic Acid), pH6.2
  At the end of the washing step, place the tube on a magnet and pipette off the supernatant carefully once the beads have migrated to the magnet and the liquid is clear
  Add immediately the anti-GPA at a concentration of 2.5 µg per mg of beads.
  Mix thoroughly by vortexing
  Incubate for 2 hours at room temperature with a slow tilt agitation or for 24 hours at 4° C.
  Place the tube on a magnet and pipette off the supernatant carefully once the beads have migrated to the magnet and the liquid is clear.
  Wash 3 times the beads with 50 mM MES buffer pH 6.2 placing the tube on the magnet.
  At the end of the washing step, resuspend the beads in a blocking buffer containing 0.3M phosphate buffer saline (PBS) with 0.5% BSA (w/v).
  Incubate for 2 hours at room temperature with a slow tilt agitation
  At the end of the blocking step, place the tube on a magnet and pipette off the supernatant carefully once the beads have migrated to the magnet and the liquid is clear.
  Remove the tube from the magnet and resuspend the beads with a preservative solution containing 0.3M PBS with 0.1% (w/v) BSA and 5% (w/v) of Synperonic™ PE/F68.

To increase the stability of the magnetic particles coupled with anti-GPA, we preferred a storage with a high concentration of Synperonic™ PE/F68 detergent, such as: 5% (w/v).

The final concentration of the beads coupled with anti-glycophorin A is 1% (w/v) in the preservative buffer. Beads are store at 4° C. until use.

B) Dilution of the Beads Coupled in the Diluents

Once the beads coupled to anti-GPA, these one are directly diluted in the diluent Liss and Ficoll™ 2% (w/v), which is then distribute on the top of the viscous solution or gel. The concentration of the beads in the diluent can vary between 0.005% and 0.02%, with a preference for 0.007%±0.001% (w/v).

EXAMPLE 15

Comparative Study in Cross Match Test (Compatibility Test) Performed on Group O Red Blood Cell Donors Showing an Increase of Sensitivity and Specificity by Reducing the Anti-GPA Concentration Coupled to the Magnetic Particles (See FIG. 17)

Group O red blood cell from donors preserved on sag-mannitol blood bags, are tested against the plasma or serum from patients likely to contain or not irregular anti-erythrocyte antibodies or against different dilutions of anti-serum of known specificities.

The test consist in a comparative study between 2 different concentrations of anti-GPA coupled to the magnetic beads and diluted in the final diluent at 0.007%.

The results are presented below.
Protocol:

From primary tube donor, 10 µl of packed red blood cells are diluted in 1 ml of low ionic strength buffer, to make a 1% erythrocyte suspension.

In the wells of a CrossLys™ (plate coated with 2 human anti-globulins (anti-IgG and anti-IgM)) 50 µl of Nanolys™ is deposited, and then 50 µl of Liss Ficoll containing magnetic beads coupled to anti-GPA is added on the Nanolys™. Add 15 µl of red blood cells diluted to 1% and finally add 15 µl of the patient's plasma or serum to be transfused. The plate is then incubated at 37° C. for 20 minutes, and then placed on a stirrer equipped with a plate of magnets fitting exactly under each well of the microplate. The final stirring under magnetic field consists in 2 sequences: 3 minutes at 500 rpm follows by 2 min at 600 rpm.

The comparative study between the 2 concentrations of anti-GPA coupled to magnetic particles shows an increase of the positive reaction size when the concentration of anti-GPA coupled is low. In the same time negative reaction are more specifics and more discriminant when this concentration is also low (i.e 2.5 µg/mg of magnetic particles).

EXAMPLE 16

Comparative Study Showing an Increase of the Stability of the Magnetic Particles when Those are Stored with High Concentration of Non Ionic Detergent: Synperonic™ PE/F68

Study Performed in Cross Match Test on Group O Red Blood Cell Donors (See FIG. 18).

Group O red blood cell from donors preserved on sag-mannitol blood bags, are tested against the plasma or serum from patients likely to contain or not irregular anti-erythrocyte antibodies or against different dilutions of anti-serum of known specificities.

The test consist in a comparative study between 2 different storage conditions of coupled magnetic particles before being diluted in the final solution.

The results are presented below.

Protocol:

From primary tube donor, 10 µl of packed red blood cells are diluted in 1 ml of low ionic strength buffer, to make a 1% erythrocyte suspension.

In the wells of a CrossLys™ (plate coated with 2 human anti-globulins (anti-IgG and anti-IgM)) 50 µl of Nanolys™ is deposited, and then 50 µl of Liss Ficoll containing magnetic beads coupled to anti-GPA is added on the Nanolys™. Add 15 µl of red blood cells diluted to 1% and finally add 15 µl of the patient's plasma or serum to be transfused. The plate is then incubated at 37° C. for 20 minutes, and then placed on a stirrer equipped with a plate of magnets fitting exactly under each well of the microplate. The final stirring under magnetic field consists in 2 sequences: 3 minutes at 500 rpm follows by 2 min at 600 rpm.

The stability study between these 2 storage conditions i.e with 0.5% or 5% of synperonic detergent shows a better stability of the beads when there are stored with 5% of synperonic before their dilution in the final solution. This is clearly demonstrate at 37° C., where in the case of the beads stored with 5% of synperonic, the positive and negative reactions are similar to the same beads stored at 4° C. While when the coupled beads are stored with only 0.5% of synperonic there is a degradation of all the reactions at 37° C.

The invention claimed is:

1. Method for the magnetization of erythrocytes, said method comprising the following steps:
   a) directly coupling of anti-glycophorin A (anti-GPA) antibody to the surface of magnetic particles, and
   b) contacting the magnetic particles coated with the anti-GPA obtained step a) with erythrocytes, wherein the anti-GPA antibody is directed against amino acids consisting of 38-44 of glycophorin A.

2. Method according to claim 1 wherein said coupling of the anti-GPA is performed by passive adsorption, by covalent coupling, by ionic hydrogen binding or by coupling type ligand-receptor.

3. Method according to claim 1 wherein said anti-GPA is a mammal antibody.

4. Method according to claim 3, wherein said anti-GPA is a mammal antibody from murine or human origin.

5. Method according to claim 1 wherein said anti-glycophorin A (anti-GPA) antibody is coupled to the surface of magnetic particles by electrostatic or hydrophobic interactions.

6. Method for the magnetization of erythrocytes, said method comprising the following steps:
   a) directly coupling of anti-glycophorin A (anti-GPA) antibody to the surface of magnetic particles, wherein, the anti-GPA antibody is directed against amino acids consisting of 38-44 of glycophorin A; and
   b) contacting the magnetic particles coated with the anti-GPA obtained step a) with erythrocytes.

SEQUENCE LISTING

<160> NUMBER OF SEQ ID NOS: 1

<210> SEQ ID NO 1
<211> LENGTH: 150
<212> TYPE: PRT
<213> ORGANISM: Homo sapiens

<400> SEQUENCE: 1

```
Met Tyr Gly Lys Ile Ile Phe Val Leu Leu Leu Ser Ala Ile Val Ser
1               5                   10                  15

Ile Ser Ala Ser Ser Thr Thr Gly Val Ala Met His Thr Ser Thr Ser
            20                  25                  30

Ser Ser Val Thr Lys Ser Tyr Ile Ser Ser Gln Thr Asn Asp Thr His
        35                  40                  45

Lys Arg Asp Thr Tyr Ala Ala Thr Pro Arg Ala His Glu Val Ser Glu
    50                  55                  60

Ile Ser Val Arg Thr Val Tyr Pro Pro Glu Glu Glu Thr Gly Glu Arg
65                  70                  75                  80

Val Gln Leu Ala His His Phe Ser Glu Pro Glu Ile Thr Leu Ile Ile
                85                  90                  95

Phe Gly Val Met Ala Gly Val Ile Gly Thr Ile Leu Leu Ile Ser Tyr
            100                 105                 110

Gly Ile Arg Arg Leu Ile Lys Lys Ser Pro Ser Asp Val Lys Pro Leu
        115                 120                 125

Pro Ser Pro Asp Thr Asp Val Pro Leu Ser Ser Val Glu Ile Glu Asn
    130                 135                 140

Pro Glu Thr Ser Asp Gln
145                 150
```

7. Method according to claim 6, wherein said anti-GPA is in a concentration from 1 µg/mg to 25 µg/mg of said magnetic particles.

* * * * *